US007184605B1

(12) United States Patent
Funahashi et al.

(10) Patent No.: US 7,184,605 B1
(45) Date of Patent: Feb. 27, 2007

(54) IMAGE NORMALIZATION PROCESSING SYSTEM

(75) Inventors: Takeshi Funahashi, Kanagawa-ken (JP); Masaaki Ohtsuka, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/281,969

(22) Filed: Mar. 31, 1999

(30) Foreign Application Priority Data

Mar. 31, 1998 (JP) ................................. 10-087361

(51) Int. Cl.
G06K 9/46 (2006.01)
(52) U.S. Cl. ........................................ 382/254; 382/260
(58) Field of Classification Search ......... 382/254–275
See application file for complete search history.

(56) References Cited

U.S. PATENT DOCUMENTS

| 4,768,099 A |   | 8/1988 | Mukai |       |
|-------------|---|--------|-------|-------|
| 6,061,465 A | * | 5/2000 | Nakajima | ................... 382/132 |
| 6,285,780 B1 | * | 9/2001 | Yamakita et al. | ........... 382/110 |
| 6,399,953 B1 | * | 6/2002 | Kitamura | .................... 250/310 |

FOREIGN PATENT DOCUMENTS

| JP | 60-086673 A | 5/1985 |
| JP | 62-18536    | 1/1987 |
| JP | 62-266680 A | 11/1987 |
| JP | 63-006672 A | 1/1988 |
| JP | 63-121986 A | 5/1988 |
| JP | 03-209574 A | 9/1991 |
| JP | 06-231244 A | 8/1994 |
| JP | 09135383 A  | * 5/1997 |
| JP | 11352617 A  | * 12/1999 |

* cited by examiner

Primary Examiner—Thomas D. Lee
Assistant Examiner—Stephen Brinich
(74) Attorney, Agent, or Firm—Sughrue Mion, PLLC

(57) ABSTRACT

Image data representing an image read by reading means are input to normalization processing condition determining means and to pre-normalization processing image inputting means of the image receiving apparatus. Parameters are input from parameter inputting means to the normalization processing condition determining means. The normalization processing condition determining means determines a normalization processing condition so that the image to be output is in an appropriate density range or the like, and inputs the condition to normalization processing condition inputting means via normalization processing condition outputting means. Normalization processing executing means normally carries out the normalization processing on the image data under a normalization processing condition which is the same as the normalization processing condition determined by the normalization processing condition determining means. When the normalization processing condition is changed, condition changing means changes the normalization processing condition to a condition different from the one determined by the normalization processing condition determining means, and the normalization processing is carried out on the image data using the condition after the change.

32 Claims, 11 Drawing Sheets

IMAGE NORMALIZATION PROCESSING SYSTEM

BACKGROUND OF THE INVENTION

1. Field of the Invention

The present invention relates to an image normalization processing system for carrying out normalization processing on an image having been read, and more specifically, to an image normalization processing system wherein a normalization processing condition determined by an image reading apparatus can be changed by an image receiving apparatus.

2. Description of the Related Art

Radiation image information reading apparatuses (CR apparatuses; Computed Radiography) which read radiation image information by detecting light emitted in accordance with the radiation image information stored on a stimulable phosphon sheet (hereinafter simply called a "sheet") upon exposure to stimulating rays, such as a laser beam irradiated on the sheet, have been known (see Japanese Unexamined Patent Publication No. 62(1987)-18536, for example). Images (image data) read by such a CR apparatus are used in a medical facility for diagnosing a lesion, injury and the like and the degree thereof by being output as visible images displayed on a CRT display or printed on a film by an LP (laser printer), for example.

In the CR apparatus, light beam scan means scans an entire sheet by using a laser beam for example, and leads the light emitted from the sheet via a light guide, to reading means comprising a photoelectric converter such as a photomultiplier tube to convert the emitted light into an electric signal (image signal). Signal processing means carries out predetermined image signal processing on the obtained image signal. By using the processed image signal, the radiation image information is output as a visible image on a recording material such as a photosensitive material or on a display apparatus such as a CRT. In this manner, a radiation image which is not affected by a change in radiation exposure can be obtained.

The signal processing means converts the image signal read by the reading means into a logarithm by using a logarithmic amplifier, for example. The image signal converted into a logarithm is then converted into digital image data by using an analog/digital converter. After desired image processing such as frequency processing or tone processing has been carried out on the image data, the signal processing means converts the image data into a TV image signal according to the NTCS system or the like, and outputs the image signal as a visible image.

Following the recent advancement in technologies for communications and computers, a system (medical network system) wherein a CR apparatus and an image receiving apparatus such as a diagnostic workstation are connected to a network has been installed in a hospital so that a computer can be used for diagnosis or the like at a location remote from the CR apparatus.

In the CR apparatus, a normalization processing condition is determined in order to cause the density or the contrast of the output visible image to be in an appropriate range. Normalization processing is carried out under the normalization processing condition on the image data read by the reading means and predetermined image processing such as frequency processing is also carried out on the image data if necessary. Based on the image data after the image processing, the visible image is output. On this occasion, after the normalization processing, image data before the normalization processing are not saved.

In a medical network system such as the one described above, image data which are obtained by image processing using a predetermined image processing condition on the normalization processing image data, or the image processing condition and the image data before the image processing, that is, the image processing condition and the post-normalization processing image data, are transferred from the CR apparatus to the image receiving apparatus.

The "normalization processing" herein referred to means signal processing for adjusting the image data read by the reading means to an input signal range of image processing means so that the visible image to be output can have an appropriate density range. For example, a condition such as a gain and a data range of the reading means (the condition set here is called a "normalization processing condition") is determined so that maximal and minimal amounts of the emitted light from a range of image information useful for diagnosis out of radiation image information read by the reading means can respectively correspond to maximal and minimal values of the appropriate density range of the output visible image and a density resolution optimal for diagnosis can also be obtained for the range of the diagnostically useful image information. Under the determined normalization processing condition, the image data read by the reading means are converted into image data to be input to the image processing means. In order to determine the "normalization processing condition", various kinds of parameters are used. More specifically, parameters which are determined based on photographing menus, such as photographing of chest and head, and are used for recognizing a pattern of the images, parameters for finding a characteristic value through generation of a histogram of image data, and the like can be listed as those parameters. As the parameters for recognizing the image pattern, partitioned photographing recognition parameters for recognizing the cases of partitioned photographing, parameters for selecting an algorithm for recognizing the case of radiation field restriction, and various kinds of radiation field recognition parameters such as radiation field detection threshold values can be listed. As for the parameters regarding a histogram, parameters for selecting an algorithm for histogram analysis or various kinds of histogram analysis parameters such as histogram analysis threshold values can be used.

The above normalization processing uses only the information corresponding to the input signal range out of the radiation image information read by the reading means, and discards all out-of-range radiation image information. Therefore, image data after normalization processing, that is, the image data to be input to the image processing means, do not include data corresponding to radiation image information which is out of the desired input signal range.

For this reason, when the normalization processing has a problem such as inappropriate setting of the desired image information range, the radiation image information once discarded cannot be restored even when the radiation image information obtained by photographing a subject and reading the image by using the reading means is appropriate. Therefore, no retrial of appropriate normalization processing using the same photographed image has been possible. In order to carry out appropriate normalization processing, the only method is to photograph again by changing the normalization processing condition. It is thus difficult to obtain radiation image information which is the same as the one read before, and this is inconvenient for diagnostic purposes.

Especially, in a medical network system, diagnosis is not carried out in parallel with reading of the image by the CR apparatus. It is generally carried out later by reading an image transferred from the CR apparatus and stored in a recording apparatus. Therefore, when there is a problem in the normalization processing carried out by the CR apparatus, the image receiving apparatus cannot solve the problem and re-photographing is rarely possible.

SUMMARY OF THE INVENTION

The present invention has been created based on consideration of the above problems, and an object of the present invention is to provide an image normalization processing system which can change a normalization processing condition determined by an image reading apparatus and carry out normalization processing again using the new normalization processing condition.

A first image normalization processing system of the present invention comprises an image reading apparatus including reading means such as a photomultiplier for reading an image to obtain image data representing the image and reading side normalization processing condition determining means for determining a normalization processing condition for the image read by the reading means, the image reading apparatus outputting the image data; and image receiving means which is connected to the image reading apparatus and includes receiving side normalization processing condition determining means for determining the normalization processing condition of the image based on the image data, and normalization processing means for carrying out normalization processing using the normalization processing condition determined by the receiving side normalization processing condition determining means on the image data.

Upon determining the "normalization processing condition", various methods can be adopted. For example, normalization processing using a predetermined normalization processing condition is actually carried out on the image data representing the image read by the reading means, and an image based on the image data after the normalization processing is displayed so that whether or not the displayed image has a desired density or contrast can be judged. The normalization processing is repeated while changing the normalization processing condition to obtain an appropriate image, and the normalization processing condition under which a desired image can be obtained is selected. Alternatively, the "normalization processing conditions" are pre-registered corresponding to a plurality of photographing menus for a subject so that a "normalization processing condition" appropriate for a photographing menu may be selected. The "photographing menu" herein referred to means the kind of photographing according to which a reading condition (normalization processing condition) needs to be changed. For example, the photographing menus mean menus classified by a body portion to be photographed or a photographing method, such as photographing of a chest or a head, or angiography.

As the "image receiving apparatus" used in the normalization processing system, any apparatus which carries out predetermined processing using image data output from the image reading apparatus can be used. For example, a diagnostic workstation which provides an image for diagnosis by displaying on a CRT the image based on the image data output from the image reading apparatus may be used. Alternatively, an LP which outputs the image on a film based on the image data output from the image reading apparatus may be used.

A second image normalization processing system of the present invention comprises an image reading apparatus including reading means for reading an image to obtain image data representing the image and reading side normalization processing condition determining means for determining a normalization processing condition for the image read by the reading means, the image reading apparatus outputting the image data and reduced image data generated from the image data by the reading side normalization processing condition determining means; and an image receiving apparatus connected to the image reading apparatus and including receiving side normalization processing condition determining means for determining a normalization processing condition of the image based on the reduced image data, and normalization processing means for carrying out normalization processing on the image data under the normalization processing condition determined by the receiving side normalization processing condition determining means.

When the normalization processing condition is normally determined, in order to shorten the operation time, the normalization processing condition is found based on the reduced image data wherein data values have been thinned, rather than based on the entire image data. As a consequence, the reduced image data are always generated when the normalization processing condition is determined. Therefore, in the present invention, the "reduced image data" are not generated intentionally, but mean data generated inevitably at the time of normalization processing condition determination by the reading side normalization processing condition determining means.

A third image normalization processing system of the present invention comprises an image reading apparatus including reading means for reading an image to obtain image data representing the image and reading side normalization processing condition determining means for determining a normalization processing condition for the image read by the reading means, the image reading apparatus outputting the image data and the normalization processing condition; and an image receiving apparatus connected to the image reading apparatus and including normalization processing means for carrying out normalization processing on the image data under the normalization processing condition and condition changing means for changing the normalization processing condition, wherein the normalization processing means is capable of carrying out normalization processing on the image data under the normalization processing condition changed by the condition changing means.

A fourth image normalization processing system of the present invention comprises an image reading apparatus including reading means for reading an image to obtain image data representing the image and reading side normalization processing condition determining means for determining a normalization processing condition for the image read by the reading means, the image reading apparatus outputting the image data and a parameter for determining the normalization processing condition; and an image receiving apparatus connected to the image reading apparatus and including receiving side normalization processing condition determining means for determining a normalization processing condition of the image based on the image data and the parameter, and normalization processing means for carrying out normalization processing on the image data under the normalization processing condition determined by the receiving side normalization processing condition determining means.

The "parameter for determining the normalization processing condition" specifically means parameters which are set according to photographing menus, such as photographing of chest and head, and are used for recognizing patterns of the images, and parameters for finding a characteristic value through generation of a histogram of the image data, for example. Based on these parameters, the normalization processing condition is determined by the reading side or the receiving side normalization processing condition determining means. As the parameters for recognizing the image patterns, partitioned photographing recognition parameters for recognizing the cases of partitioned photographing, parameters for selecting an algorithm for recognizing the case of radiation field restriction, and various kinds of radiation field recognition parameters such as radiation field detection threshold values can be listed. As the parameters regarding a histogram, parameters for selecting an algorithm for histogram analysis and various kinds of histogram analysis parameters such as histogram analysis threshold values can be used.

A fifth image normalization processing system of the present invention comprises an image reading apparatus including reading means for reading an image to obtain image data representing the image and reading side normalization processing condition determining means for determining a normalization processing condition for the image read by the reading means, the image reading apparatus outputting the image data, reduced image data generated from the image data by the reading side normalization processing condition determining means, and a parameter for determining the normalization processing condition; and an image receiving apparatus connected to the image reading apparatus and including receiving side normalization processing condition determining means for determining a normalization processing condition of the image based on the reduced image data and the parameter, and normalization processing means for carrying out normalization processing on the image data under the normalization processing condition determined by the receiving side normalization processing condition determining means.

A sixth image normalization processing system of the present invention comprises an image reading apparatus including reading means for reading an image to obtain image data representing the image and reading side normalization processing condition determining means for determining a normalization processing condition for the image read by the reading means, the image reading apparatus outputting the image data, the normalization processing condition, and a parameter for determining the normalization processing; and an image receiving apparatus connected to the image reading apparatus and including normalization processing means for carrying out normalization processing on the image data under the normalization processing condition and condition changing means for changing the normalization processing condition based on the parameter, wherein the normalization processing means is capable of carrying out normalization processing on the image data under the normalization processing condition changed by the condition changing means.

A seventh image normalization processing system of the present invention comprises an image reading apparatus including reading means for reading an image to obtain image data representing the image and reading side normalization processing condition determining means for determining a normalization processing condition for the image read by the reading means, the image reading apparatus outputting the image data, the normalization processing condition, and reduced image data generated from the image data by the reading side normalization processing condition determining means; and an image receiving apparatus connected to the image reading apparatus and including normalization processing means for carrying out normalization processing on the image data under the normalization processing condition and condition changing means for changing the normalization processing condition based on the reduced image data, wherein the normalization processing means is capable of carrying out normalization processing on the image data under the normalization processing condition changed by the condition changing means.

An eighth image normalization processing system of the present invention comprises an image reading apparatus including reading means for reading an image to obtain image data representing the image and reading side normalization processing condition determining means for determining a normalization processing condition for the image read by the reading means, the image reading apparatus outputting the image data, the normalization processing condition, reduced image data generated from the image data by the reading side normalization processing condition determining means, and a parameter for determining the normalization processing condition; and an image receiving apparatus connected to the image reading apparatus and including normalization processing means for carrying out normalization processing on the image data under the normalization processing condition and condition changing means for changing the normalization processing condition based on the reduced image data and the parameter, wherein the normalization processing means is capable of carrying out normalization processing on the image data under the normalization processing condition changed by the condition changing means.

A ninth image normalization processing system of the present invention is any one of the first to eighth image normalization processing system comprising the image reading apparatus further including judging means for judging whether or not the normalization processing condition determined by the reading side normalization processing condition determining means is within a predetermined range, the image reading apparatus outputting at least one of the image data, the normalization processing condition, the reduced image data, and the parameter to the image receiving apparatus if the normalization processing condition has been judged to be not in the predetermined range and otherwise carrying out the normalization processing on the image data to output the normalized image data to the image receiving apparatus. In this case, depending on which of the image data, the normalization processing condition, the reduced image data, and the parameter has been input to the image receiving apparatus, the image receiving apparatus carries out the processing corresponding to the first to eighth image normalization processing system to obtain the receiving side normalization processing condition, and the normalization processing is carried out on the image data under the receiving side normalization processing condition. The normalization processing conditions obtained by the image reading apparatus and the image receiving apparatus are different. However, in some cases, the conditions obtained by both of the apparatuses are the same.

In a radiation image, an area of diagnostic interest exists for each photographed body portion or photographing menu. For example, the area of the lungs is the area of interest in the case of simple chest photographing. The area of interest needs to have an appropriate density depending on the purpose of diagnosis. A value can be set for each area of interest as an optimal density. (For example, 1.0~1.2 is the appropriate density for the lungs.) For this reason, the image data normalized by using the normalization processing condition need to fall within the predetermined range so that the density of the area of interest becomes optimal. Therefore, that "the normalization processing condition is within a predetermined range" means that the density of the area of interest falls within an optimal density range in accordance with the photographed body portion or the photographing menu, when the image data are normalized by using the normalization processing condition determined by the reading side normalization processing condition determining means.

A tenth image normalization processing system of the present invention comprises an image reading apparatus including reading means for reading an image to obtain image data representing the image, reading side normalization processing condition determining means for determining a first normalization processing condition for the image read by the reading means, and reading side normalization processing means for carrying out normalization processing on the image data, the image reading apparatus outputting reduced image data generated from the image data by the reading side normalization processing condition determining means; and an image receiving apparatus connected to the image reading apparatus and including receiving side normalization processing condition determining means for determining a second normalization processing condition based on the reduced image data, wherein the second normalization processing condition is output to the image reading apparatus and the reading side normalization processing means carries out normalization processing on the image data under the second normalization processing condition to generate normalized image data to be output to the image receiving apparatus.

An eleventh image normalization processing system of the present invention comprises an image reading apparatus including reading means for reading an image to obtain image data representing the image and reading side normalization processing condition determining means for determining a normalization processing condition for the image read by the reading means, the image reading apparatus outputting the image data and the normalization processing condition; and an image receiving apparatus connected to the image reading apparatus and including judging means for judging whether or not the normalization processing condition is within a predetermined range and normalization processing means for carrying out normalization processing on the image data under the normalization processing condition if the normalization processing condition has been judged to be in the predetermined range and canceling means for canceling the normalization processing on the image data by the normalization processing means under the normalization processing condition if the normalization processing condition has been judged to be not in the predetermined range.

It is preferable for the eleventh image normalization processing system of the present invention to further comprise warning means for issuing a warning when the normalization processing is canceled by the canceling means.

As the "warning", cancellation of the normalization processing may be displayed on display means such as a CRT of the image receiving apparatus, or the cancellation may be notified by an audio message or an alarm.

It is preferable for the eleventh image normalization processing system of the present invention to further comprise condition changing means for changing the normalization processing condition so that the condition changing means changes the normalization processing condition when the canceling means cancels the normalization processing, and the normalization processing means carries out normalization processing on the image data under the normalization processing condition having been changed.

An image output method of the present invention outputs image data to an image receiving apparatus from an image reading apparatus comprising reading means for reading an image to obtain the image data representing the image and normalization processing condition determining means for determining a normalization processing condition for the image having been read by the reading means.

It is preferable for the image output method of the present invention to output to the image receiving apparatus at least one of the normalization processing condition, reduced image data generated from the image data by the normalization processing condition determining means, and a parameter for determining the normalization processing condition, in addition to the image data.

It is also preferable for the image output method of the present invention to judge whether or not the normalization processing condition is within a predetermined range, and to output to the image receiving apparatus at least one of the normalization processing condition, the reduced image data generated from the image data by the normalization processing condition determining means, and the parameter for determining the normalization processing condition in addition to the image data, when the normalization processing condition is not within the predetermined range.

According to the first image normalization processing system of the present invention, not the normalized image data but the image data before normalization processing (pre-normalization processing image data) are input from the image reading apparatus to the image receiving apparatus although the normalization processing condition is determined by the image reading apparatus, and the image receiving apparatus can determine the normalization processing condition based on the image data and can carry out normalization processing under the determined normalization processing condition. Therefore, the normalization processing condition is appropriately changed by the image receiving apparatus, and a medical network system with improved convenience can be provided.

According to the second image normalization processing system of the present invention, the image data before normalization processing and the reduced image data generated by the reading side normalization processing condition determining means are input from the image reading apparatus to the image receiving apparatus, and the image receiving apparatus can determine the normalization processing condition based on the reduced image data and can carry out normalization processing under the determined normalization processing condition. Therefore, the image receiving apparatus can carry out normalization processing while appropriately changing the normalization processing condition. Furthermore, since it is not necessary for the receiving side normalization processing condition determining means to generate the reduced image data from the image data, an operation time for determining the normalization processing condition can be shortened.

According to the third image normalization processing system of the present invention, image data before normalization processing and the normalization processing condition are input from the image reading apparatus to the image receiving apparatus, and the image receiving apparatus can normally carry out normalization processing under the normalization processing condition which is input for the image data before normalization processing and can change the normalization processing condition if necessary to carry out the normalization processing under the normalization processing condition having been changed. Therefore, when there is a problem in the normalization processing carried out under the input normalization processing condition, the normalization processing can be carried out again by using the normalization processing condition having been changed to solve the problem. In this manner, a problem in the normalization processing can be solved. Even when there is no problem in the normalization processing, the normalization processing condition can be changed appropriately if an image under a different normalization processing condition needs to be viewed. In this manner, a medical network system with improved convenience can be provided.

According to the fourth image normalization processing system of the present invention, the image data before normalization processing and the parameter for determining the normalization processing condition are input from the image reading apparatus to the image receiving apparatus, and the image receiving apparatus can determine the normalization processing condition based on the image data and the parameter and can carry out normalization processing under the determined normalization processing condition. Therefore, the image receiving apparatus can carry out normalization processing while appropriately changing the normalization processing condition. Furthermore, since it is not necessary for the image receiving apparatus to retain the parameters to determine the normalization processing condition, storing means for storing the parameters can be saved and the configuration of the image receiving apparatus can be made simpler.

According to the fifth image normalization processing system of the present invention, the image data before normalization processing, the reduced image data generated by the reading side normalization processing condition determining means, and the parameter are input from the image reading apparatus to the image receiving apparatus, and the image receiving apparatus can determine the normalization processing condition based on the reduced image data and the parameter, and can carry out normalization processing under the determined normalization processing condition. Therefore, the image receiving apparatus can carry out the normalization processing while appropriately changing the normalization processing condition. Furthermore, since it is not necessary for the receiving side normalization processing condition determining means to generate the reduced image data from the image data, an operation time for determining the normalization processing condition can be shortened. Moreover, since it is not necessary for the image receiving apparatus to retain the parameters to determine the normalization processing condition, storing means for storing the parameter can be saved and the configuration of the image receiving apparatus can be made simpler.

According to the sixth image normalization processing system of the present invention, image data before normalization processing, the normalization processing condition, and the parameter are input from the image reading apparatus to the image receiving apparatus, and the image receiving apparatus can normally carry out normalization processing under the normalization processing condition which is input for the image data before normalization processing and can change the normalization processing condition based on the parameter if necessary to carry out the normalization processing under the normalization processing condition having been changed. Therefore, when there is a problem in the normalization processing carried out under the input normalization processing condition, the normalization processing can be carried out again by using the normalization processing condition having been changed to solve the problem. In this manner, a problem in the normalization processing can be solved. Even when there is no problem in the normalization processing, the normalization processing condition can be changed appropriately. Therefore, a medical network system with improved convenience can be provided. Moreover, since it is not necessary for the image receiving apparatus to retain the parameters to determine the normalization processing condition, storing means for storing the parameters can be saved and the configuration of the image receiving apparatus can be made simpler.

According to the seventh image normalization processing system of the present invention, the image data before normalization processing, the normalization processing condition, and the reduced image data are input from the image reading apparatus to the image receiving apparatus, and the image receiving apparatus can normally carry out normalization processing under the normalization processing condition which is input for the image data before normalization processing and can change the normalization processing condition if necessary based on the reduced image data in order to carry out the normalization processing under the normalization processing condition having been changed. Therefore, when there is a problem in the normalization processing carried out under the input normalization processing condition, the normalization processing can be carried out again by using the normalization processing condition having been changed to solve the problem. In this manner, a problem in the normalization processing can be solved. Even when there is no problem in the normalization processing, the normalization processing condition can be changed discretionarily. Therefore, a medical network system with improved convenience can be provided. Furthermore, since it is not necessary for the receiving side normalization processing condition determining means to generate the reduced image data from the image data, an operation time for determining the normalization processing condition can be shortened.

According to the eighth image normalization processing system of the present invention, the image data before normalization processing, the normalization processing condition, the reduced image data, and the parameter are input from the image reading apparatus to the image receiving apparatus, and the image receiving apparatus can normally carry out normalization processing under the normalization processing condition which is input for the image data before normalization processing and can change the normalization processing condition if necessary based on the reduced image data and the parameter in order to carry out the normalization processing under the normalization processing condition having been changed. Therefore, when there is a problem in the normalization processing carried out under the input normalization processing condition, the normalization processing can be carried out again by adopting the normalization processing condition having been changed to solve the problem. In this manner, a problem in the normalization processing can be solved. Even when there is no problem in the normalization processing, the normalization processing condition can be changed at the user's discretion. Therefore, a medical network system with improved convenience can be provided. Furthermore, since it is not necessary for the receiving side normalization processing condition determining means to generate the reduced image data from the image data, an operation time for determining the normalization processing condition can be shortened. Moreover, since it is not necessary for the image receiving apparatus to retain the parameters to determine the normalization processing condition, storing means for storing the parameters can be saved and the configuration of the image receiving apparatus can be made simpler.

The ninth image normalization processing system of the present invention is any one of the first to eighth image normalization processing system whose image reading apparatus judges whether or not the normalization processing condition is within the predetermined range. When the normalization processing condition is within the predetermined range, the image reading apparatus carries out normalization processing on the image data and outputs the normalized image data to the image receiving apparatus. When the normalization processing condition is not within the predetermined range, the image reading apparatus outputs to the image receiving apparatus at least one of the image data before normalization processing, the normalization processing condition, the reduced image data, and the parameter, and the image receiving apparatus carries out the same normalization processing as is carried out by the first to eighth image normalization processing system in accordance with which of the normalization processing condition, the reduced image data, and the parameter have been input thereto. Therefore, the normalized image data are only input to the image receiving apparatus when a desired normalization processing has been carried out, and the image data before normalization processing, the normalization processing condition, the reduced image data, and the parameter are not input to the image receiving apparatus in the case where no change in the normalization processing is needed. In this manner, efficient data transfer can be carried out. Furthermore, since the image data before normalization, the normalization processing condition, the reduced image data, and the parameter are only input in the case where a desired normalization processing has not been carried out, the normalization processing condition can be changed appropriately. Therefore, a medical network system with improved convenience can be provided.

According to the tenth image normalization processing system of the present invention, only the reduced image data generated by the reading side normalization processing condition determining means are input to the image receiving apparatus, and the image receiving apparatus determines the normalization processing condition based on the reduced image data. The normalization processing condition determined by the image receiving apparatus (the second normalization processing condition) is then input to the image reading apparatus and the image reading apparatus obtains the normalized image data by carrying out normalization processing on the image data under the second normalization processing condition to input the normalized image data to the image receiving apparatus. Therefore, since the image receiving apparatus does not need to comprise normalization processing means for carrying out normalization processing, the configuration of the image receiving apparatus becomes simpler. Furthermore, since only the reduced image data in small data size are first transferred from the image reading apparatus, the data transfer time can be shortened and processing efficiency is improved. Moreover, since the image receiving apparatus can appropriately change the normalization processing condition, a medical network system with improved convenience can be provided.

According to the eleventh image normalization processing system of the present invention, the image data before normalization processing and the normalization processing condition are input from the image reading apparatus to the image receiving apparatus. The image receiving apparatus judges whether or not the normalization processing condition is within the predetermined range, and carries out the normalization processing condition on the image data under the input normalization processing condition when the normalization processing condition has been judged to be in the predetermined range, and otherwise cancels the normalization processing. Therefore, no normalization processing is carried out under a problematic normalization processing condition, and unnecessary normalization processing is prevented from being carried out.

In this case, by issuing a warning notifying cancellation of the normalization processing, an operator can be made aware of the cancellation of the processing.

Furthermore, when the normalization processing has been canceled, normalization processing is carried out on the image data under the normalization processing condition changed by the condition changing means. In this manner, normalization processing can be carried out again adopting the normalization processing condition having been changed to solve the problem in the case where the normalization processing condition is problematic. In this manner, a problem in the normalization processing condition can be solved.

DESCRIPTION OF THE PREFERRED EMBODIMENTS

Hereinafter, embodiments of an image normalization processing system of the present invention will be explained with reference to the accompanying drawings.

Figure 1:
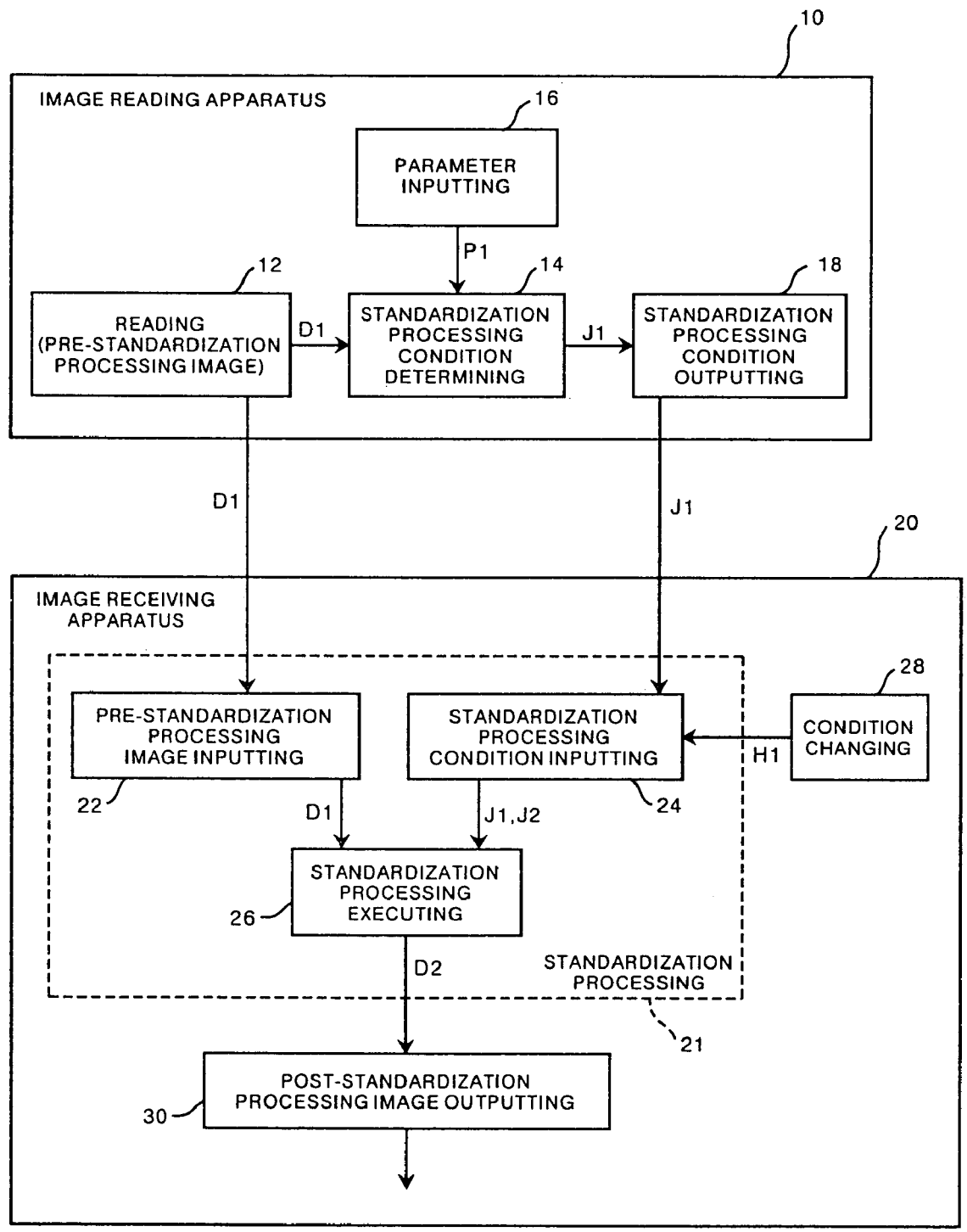
FIG. 1 is a diagram showing a configuration of an image normalization processing system according to a first embodiment of the present invention.

FIG. 1 shows a configuration of an image normalization processing system according to a first embodiment of the present invention. The image normalization processing system comprises an image reading apparatus 10 and an image receiving apparatus 20, both of which are connected to each other.

The image reading apparatus 10 comprises reading means 12 such as a photomultiplier for reading a subject image and for obtaining image data D1 representing the image, normalization processing condition determining means 14 for determining a normalization processing condition J1 for the image data D1, parameter inputting means 16 for inputting a parameter P1 for determination of the normalization processing condition to the normalization processing condition determining means 14, and normalization processing condition outputting means 18 for receiving the normalization processing condition J1 determined by the normalization processing condition determining means 14 and for outputting the normalization processing condition to the image receiving apparatus 20. The image data D1 are image data before normalization processing.

The image receiving apparatus 20 comprises normalization processing means 21 including pre-normalization processing image inputting means 22 for receiving the image data D1, normalization processing condition inputting means 24 for receiving the normalization processing condition J1 output from the normalization processing condition outputting means 18 of the image reading apparatus 10, and normalization processing executing means 26 for carrying out normalization processing using the normalization processing condition J1 output from the normalization processing condition inputting means 24 on the image data D1 output from the pre-normalization processing image inputting means 22 and for obtaining the normalized image data D2, condition changing means 28 for issuing a condition change command H1 to change the normalization processing condition J1 output from the normalization processing condition inputting means 24, and post-normalization processing image outputting means 30 for receiving the normalized image data D2 and for outputting the normalized image data D2 to image processing means which is not shown.

An operation of the image normalization processing system according to the first embodiment will be explained next. In the image reading apparatus 10, the image data D1 are obtained from a subject image photographed and read by the reading means 12, and are input to the normalization processing condition determining means 14 and to the pre-normalization processing image inputting means 22 of the image receiving apparatus 20.

The parameters P1 for setting the normalization processing condition J1 such as maximal and minimal amounts of emitted light from a desired portion of the subject image read by the reading means 12, maximal and minimal values of an appropriate density range, and maximal and minimal signal levels of a desired input signal range are input from the parameter inputting means 16 to the normalization processing condition determining means 14.

The normalization processing condition determining means 14 changes the parameters P1 input from the parameter inputting means 16, and determines, while changing the parameters P1, the normalization processing condition J1 such that a visible image after the normalization processing on the image data D1 under the normalization processing condition J1 is in the appropriate density range and contrast (that is, "determines the normalization processing condition"). When determining the normalization processing condition, various methods can be used. For example, as has been described above, the normalization processing condition may be determined after carrying out actual normalization processing, or by selecting the normalization processing condition corresponding to a photographing menu out of pre-registered normalization processing conditions.

The normalization processing condition determining means 14 outputs the determined normalization processing condition J1 to the normalization processing condition outputting means 18. The normalization processing condition outputting means 18 outputs the normalization processing condition J1 having been received thereby to the image receiving apparatus 20.

In the image receiving apparatus 20, the pre-normalization processing image data D1 are obtained by the pre-normalization processing image inputting means 22 and the normalization processing condition J1 output from the normalization processing condition outputting means 18 are also obtained by the normalization processing condition inputting means 24.

The normalization processing executing means 26 carries out the normalization processing using the normalization processing condition J1 on the image data D1 to obtain the normalized image data D2. The normalized image data D2 are output to the image processing means via the post-normalization processing image outputting means 30.

The normalization processing condition outputting means 18 and the normalization processing condition inputting means 24 serve as interfaces for the normalization processing condition J1 between the image reading apparatus 10 and the image receiving apparatus 20. In this manner, the normalized image data D2, which are the image data normally subjected to normalization processing under the normalization processing condition J1 determined by the image reading apparatus 10, are output from the post-normalization processing image outputting means 30.

Meanwhile, the condition change command H1 can be input from the condition changing means 28 to the normalization processing condition inputting means 24. When the condition change command H1 is issued from the condition changing means 28, in accordance with the condition change command H1, the normalization processing condition inputting means 24 changes the normalization processing condition J1 to be output therefrom to a parameter value different from the normalization processing condition J1 having been input thereto, in order to obtain a normalization processing condition J2. The parameters used for determination of the normalization processing condition J2 are retained in the image receiving apparatus 20, as in the parameter inputting means 16 of the image reading apparatus 10.

Therefore, in the first embodiment, normalization processing can be carried out normally under the normalization processing condition J1 determined by the image reading apparatus 10. When the normalization processing carried out under the normalization processing condition J1 encounters a problem, for example, the condition changing means 28 changes the normalization processing condition J1 output from the normalization processing condition inputting means 24 to normalization processing condition J2 that is different from the normalization processing condition J1 in order to solve the problem. The normalization processing executing means 26 executes the normalization processing again on the image data D1 under the normalization processing condition J2 after the change, and the normalized image data D2 on which appropriate normalization processing has been carried out can be output from the post-normalization processing image outputting means 30. Therefore, according to the normalization processing system having the above configuration, when normalization processing encounters a problem, the problem can be solved.

Figure 2:
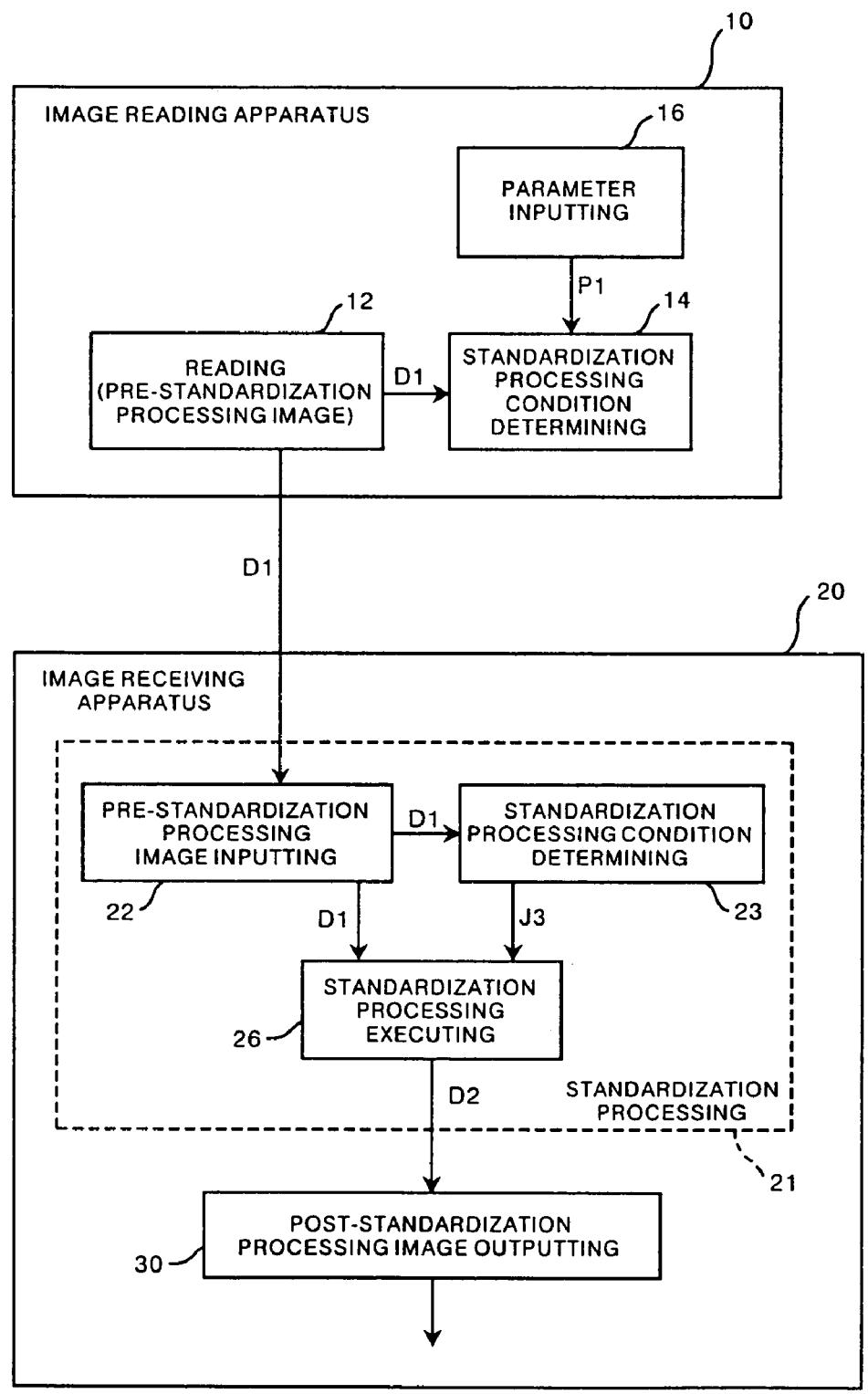
FIG. 2 is a diagram showing a configuration of an image normalization processing system according to a second embodiment of the present invention.

A second embodiment of the present invention will be explained next. FIG. 2 shows a configuration of an image normalization processing system according to the second embodiment of the present invention. As in the first embodiment, in the second embodiment, the image normalization processing system comprises an image reading apparatus 10 and an image receiving apparatus 20 both of which are connected to each other. In the embodiments which will be explained hereinafter, the same components as in the first embodiment have the same reference numerals and detailed explanation thereof will be omitted.

The image reading apparatus 10 comprises reading means 12, normalization processing condition determining means 14, and parameter inputting means 16. However, the image reading apparatus does not include normalization processing condition outputting means.

The image receiving apparatus 20 comprises normalization processing means 21 including pre-normalization processing image inputting means 22, normalization processing executing means 26, and normalization processing condition determining means 23 for determining a normalization processing condition J3 for image data D1 based on the image data D1 output from the pre-normalization processing image inputting means 22, and post-normalization processing image outputting means 30. In the image receiving apparatus 20, parameters for determining the normalization processing condition J3 are retained as in the parameter inputting means 16 of the image reading apparatus 10.

Hereinafter, an operation of the normalization processing system according to the second embodiment will be explained. The reading means 12 of the image reading apparatus 10 obtains the image data D1 and inputs the image data D1 to the normalization processing condition determining means 14 while outputting the image data to the image receiving apparatus 20. The normalization processing condition determining means 14 determines the normalization processing condition J1 based on parameters P1 input from the parameter inputting means 16. However, in the second embodiment, the normalization processing condition J1 is not output to the image receiving apparatus 20.

In the image receiving apparatus 20, the image data D1 are input to the normalization processing condition determining means 23 and the normalization processing executing means 26. In the normalization processing condition determining means 23, as in the normalization processing condition determining means 14 of the image reading apparatus 10, the normalization processing condition J3 is determined based on the image data D1 as well as the normalization processing condition determining parameters retained in the image receiving apparatus 20.

The normalization processing executing means 26 carries out normalization processing on the image data D1 under the normalization processing condition J3 output from the normalization processing condition determining means 23 in order to obtain image data D2. The image data D2 are output to image processing means via the post-normalization processing image outputting means 30.

Therefore, in the second embodiment, the normalization processing condition J1 determined in the image reading apparatus 10 is not input to the image receiving apparatus 20, and only the image data D1 before normalization processing obtained by the reading means 12 are input. In the image receiving apparatus 20, the normalization processing condition J3 is determined based on the image data D1, and normalization processing is carried out on the image data D1 under the normalization processing condition J3. Therefore, normalization processing can be carried out by the image receiving apparatus 20 while the normalization processing condition is appropriately changed. In this manner, a medical network system with improved convenience can be provided.

Figure 3:
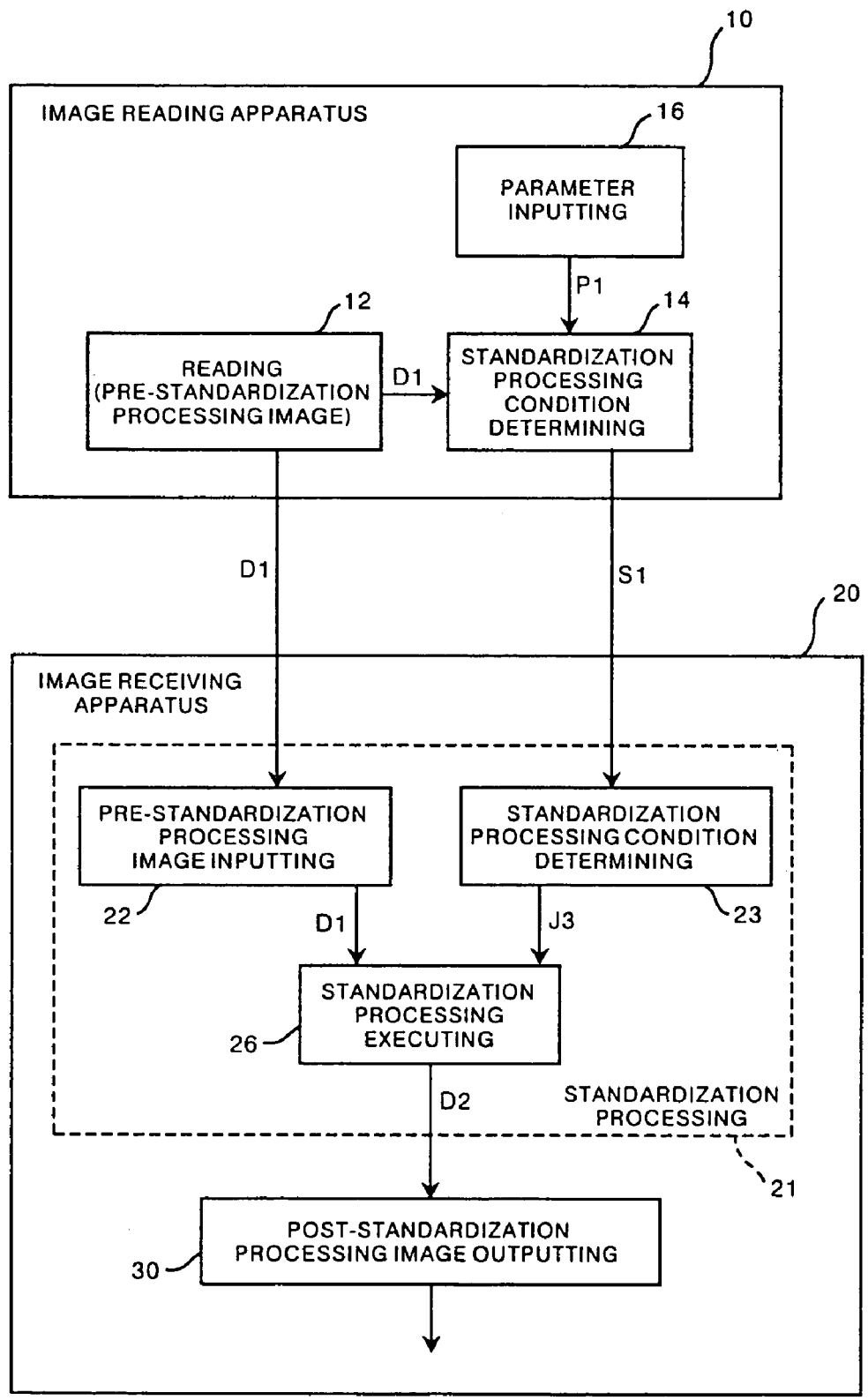
FIG. 3 is a diagram showing a configuration of an image normalization processing system according to a third embodiment of the present invention.

A third embodiment of the present invention will be explained next. FIG. 3 shows a configuration of an image normalization processing system according to the third embodiment of the present invention. The third embodiment has the same configuration as the second embodiment. However, reduced image data S1 generated upon determination of a normalization processing condition J1 by normalization processing condition determining means 14 of an image reading apparatus 10 are input to normalization processing condition determining means 23 of an image receiving apparatus 20, and the normalization processing condition determining means 23 determines a normalization processing condition J3 based on the reduced image data S1. In the image receiving apparatus 20, parameters for determining the normalization processing condition J3 are retained, as in parameter inputting means 16 of the image reading apparatus 10.

In other words, in order to shorten an operation time for determining the normalization processing condition, the normalization processing condition is normally determined based on the reduced image data wherein data values have been thinned, rather than based on the entire image data. Therefore, when the normalization processing condition is determined, the reduced image data are necessarily generated. Consequently, the reduced image data S1 originated from the image data D1 are generated as a matter of course by the normalization processing condition determining means 14 of the image reading apparatus 10. The reduced image data S1 are input to the normalization processing condition determining means 23 of the image receiving apparatus 20 and the normalization processing condition J3 is determined by the normalization processing condition determining means 23 based on the reduced image data S1 as well as the normalization processing condition determining parameters retained in the image receiving apparatus 20. Therefore, in the third embodiment, since it is not necessary for the normalization processing condition determining means 23 to generate the reduced image data S1 from the image data D1, the operation time for determining the normalization processing condition J3 is shortened.

Figure 4:
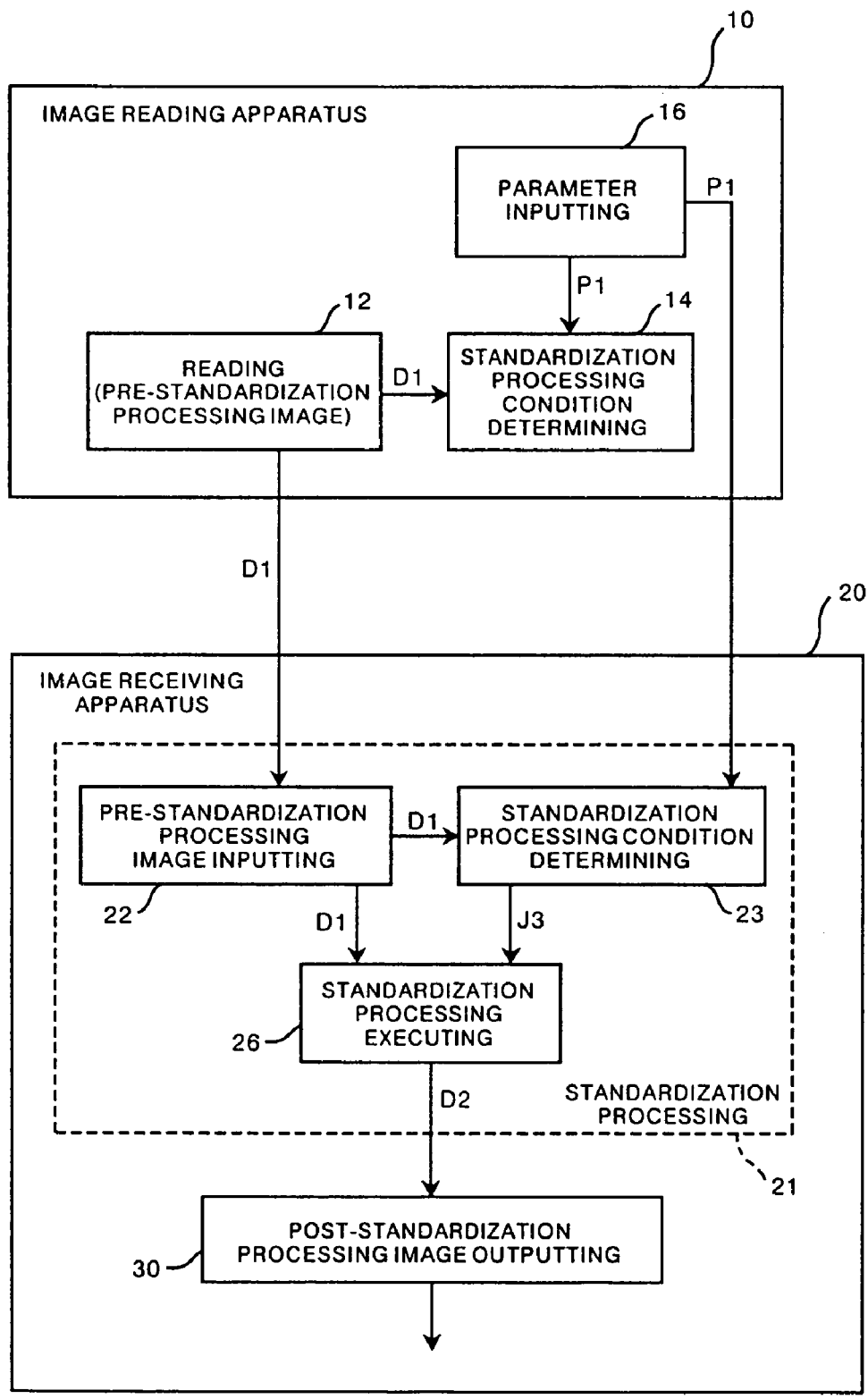
FIG. 4 is a diagram showing a configuration of an image normalization processing system according to a fourth embodiment of the present invention.

A fourth embodiment of the present invention will be explained below. FIG. 4 shows a configuration of an image normalization processing system according to the fourth embodiment of the present invention. The fourth embodiment has the same configuration as the second embodiment. However, parameters P1 output from parameter inputting means 16 of an image reading apparatus 10 are input to normalization processing condition determining means 23 of an image receiving apparatus 20 and the normalization processing condition determining means 23 determines a normalization processing condition J3 based on the image data D1 and the parameters P1.

As has been described above, in the fourth embodiment, the normalization processing condition J3 is determined based on the parameters P1 input from the parameter inputting means 16 of the image reading apparatus 10 for determination of the normalization processing condition J3. Therefore, it is not necessary for the image receiving apparatus 20 to retain the parameters for determining the normalization processing condition, and means for storing the parameters can be saved. In this manner, the configuration of the image receiving apparatus 20 can be made simpler.

Figure 5:
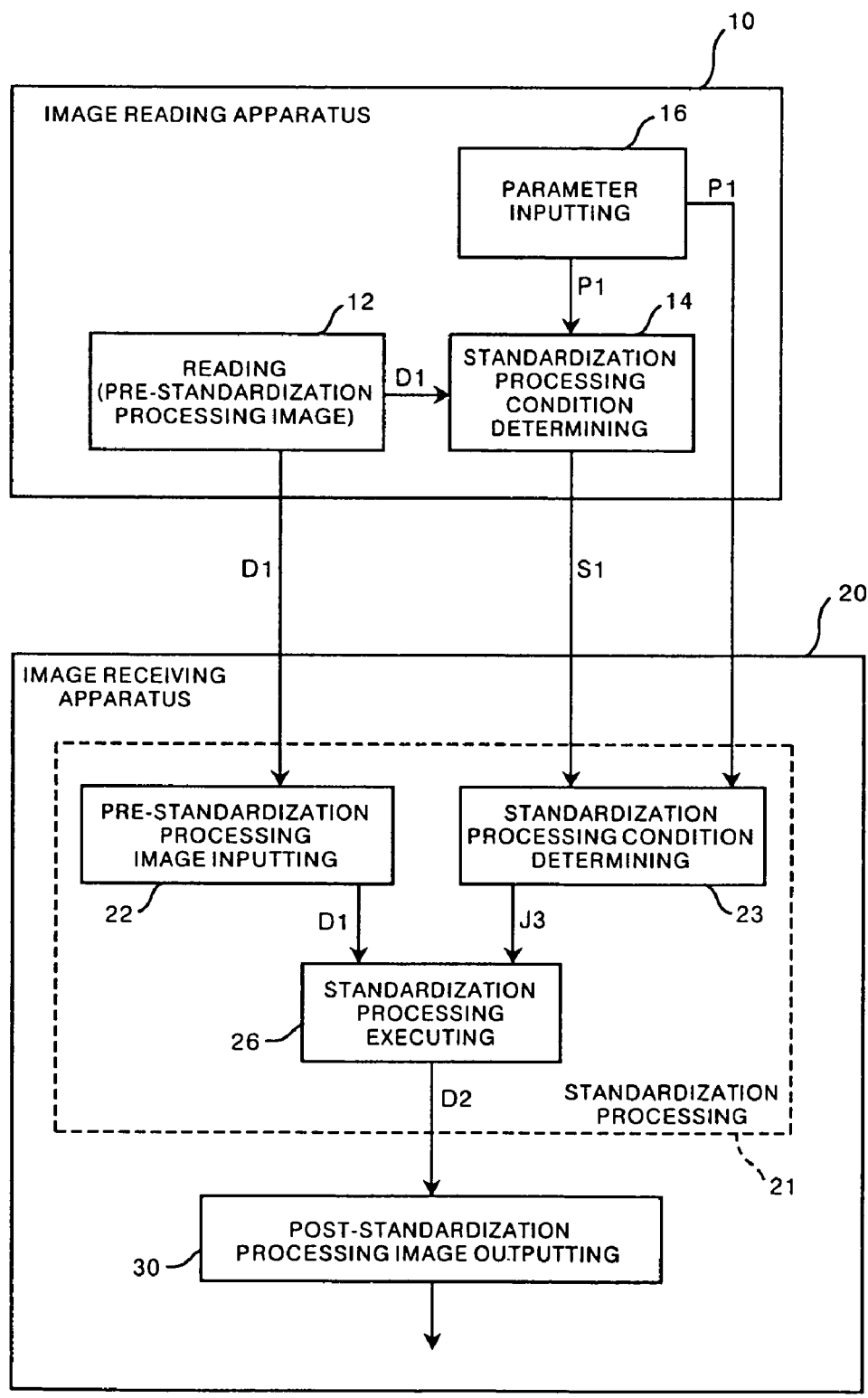
FIG. 5 is a diagram showing a configuration of an image normalization processing system according to a fifth embodiment of the present invention.

A fifth embodiment of the present invention will be explained next. FIG. 5 shows a configuration of an image normalization processing system according to the fifth embodiment of the present invention. The fifth embodiment has the same configuration as the fourth embodiment. However, reduced image data S1 generated upon determination of a normalization processing condition J1 by normalization processing condition determining means 14 of an image reading apparatus 10 are input to normalization processing condition determining means 23 of an image receiving apparatus 20, and the normalization processing condition determining means 23 determines a normalization processing condition J3 based on the reduced image data S1 and parameters P1.

As has been described above, in the fifth embodiment, the normalization processing condition J3 is determined based on the parameters P1 input from parameter inputting means 16 of the image reading apparatus 10 for determination of the normalization processing condition J3. Therefore, it is not necessary for the image receiving apparatus 20 to retain the parameters for determination of the normalization processing condition, and means for storing the parameters can be saved. As a result, the configuration of the image receiving apparatus 20 can be made simpler. Furthermore, since it is not necessary for the normalization processing condition determining means 23 to generate the reduced image data S1 from the image data D1 upon determination of the normalization processing condition J3, an operation time for determining the normalization processing condition J3 can be shortened.

Figure 6:
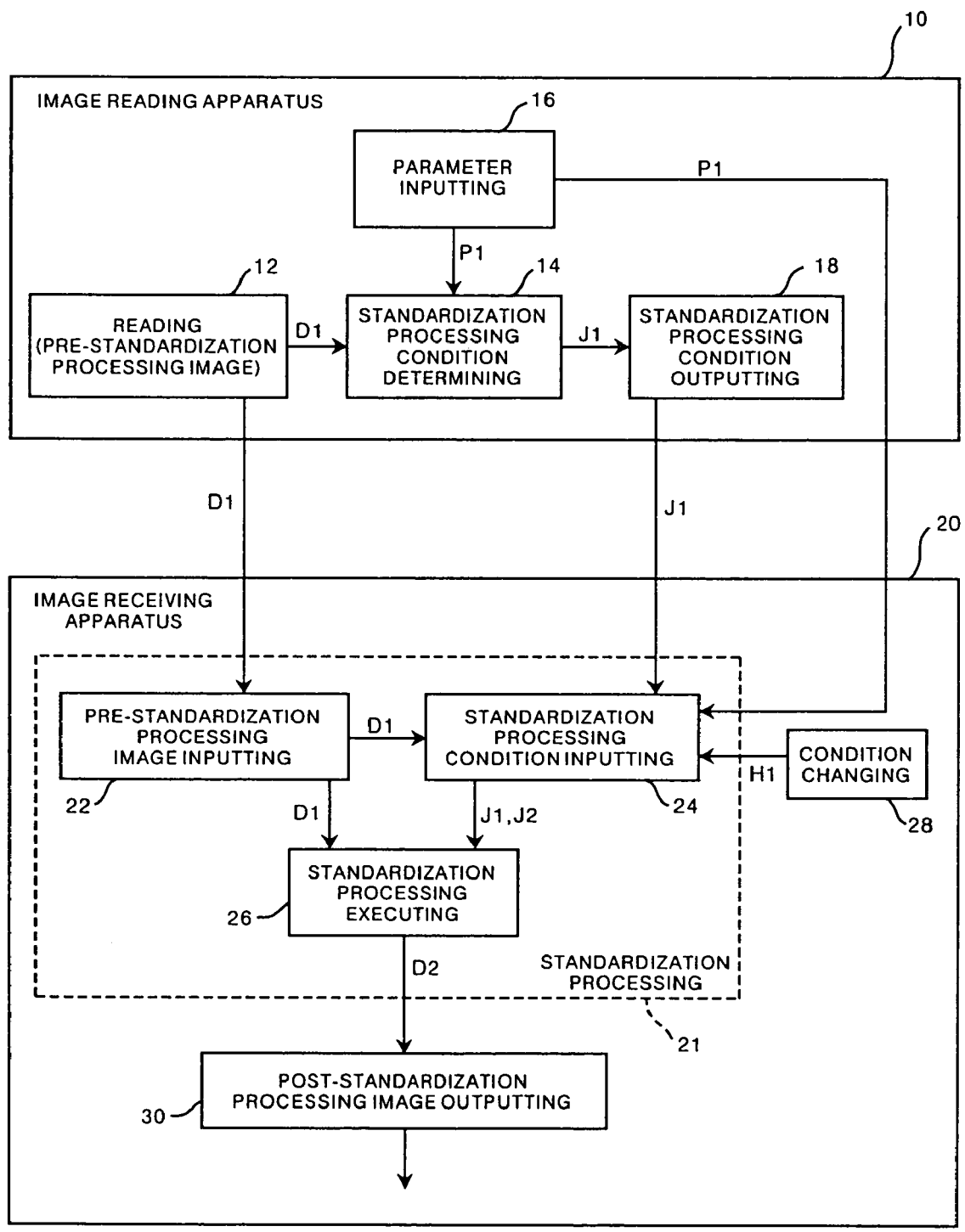
FIG. 6 is a diagram showing a configuration of an image normalization processing system according to a sixth embodiment of the present invention.

A sixth embodiment of the present invention will be explained next. FIG. 6 shows a configuration of an image normalization processing system according to the sixth embodiment. The sixth embodiment has the same configuration as the first embodiment. However, parameters P1 output from parameter inputting means 16 of an image reading apparatus 10 are input to normalization processing condition inputting means 24 of an image receiving apparatus 20 and a normalization processing condition J1 is changed by the normalization processing condition inputting means 24 to obtain a normalization processing condition J2 based on the parameters P1 and image data D1 when a condition change command H1 is issued.

In the sixth embodiment, normalized image data D2 are normally obtained by carrying out normalization processing on the image data D1 under the normalization processing condition J1 output from normalization processing condition outputting means 18. When the condition change command H1 is issued from condition changing means 28, the normalization processing condition J2 is obtained by the normalization processing condition inputting means 24 in response to the condition change command H1, by changing the normalization processing condition J1 output from the normalization processing condition inputting means 24 based on the image data D1 and the parameters P1 input to the image receiving apparatus 20. The normalized image data D2 are obtained by carrying out normalization processing on the image data D1 by using normalization processing executing means 26 under the normalization processing condition J2 having been changed.

Therefore, in the sixth embodiment, when the normalization processing carried out under the normalization processing condition J1 has a problem, the normalization processing condition J1 can be changed to solve the problem to the normalization processing condition J2 different from the normalization processing condition J1, and the normalization processing can be carried out again under the changed normalization processing condition J2, as in the first embodiment. Therefore, the normalized image data D2 whereon normalization processing has been carried out appropriately can be output from post-normalization processing image outputting means 30. Furthermore, in the sixth embodiment, it is not necessary for the image receiving apparatus 20 to retain the parameters for determination of the normalization processing condition. Therefore, means for storing the parameters can be saved and the configuration of the image receiving apparatus 20 becomes simpler.

Figure 7:
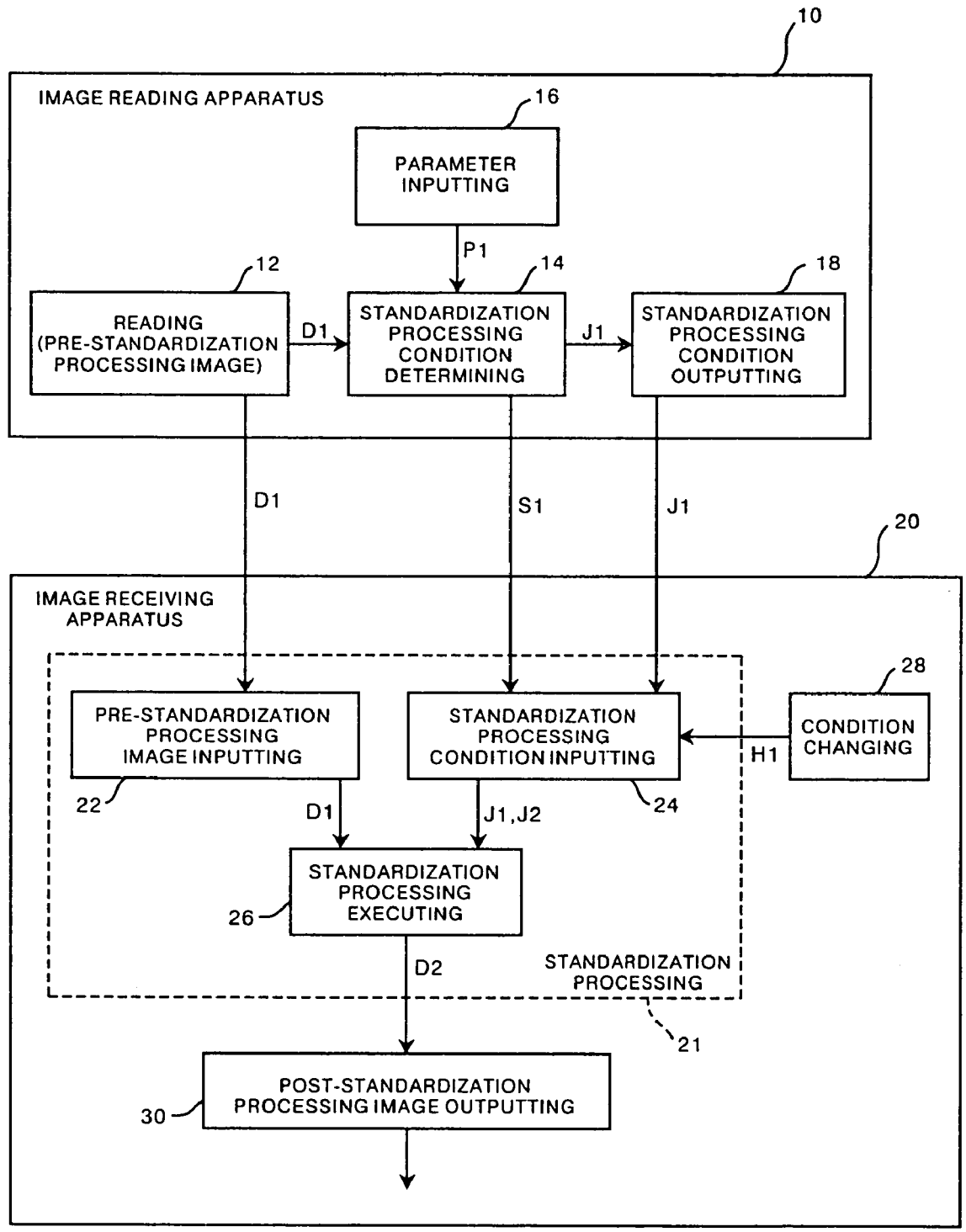
FIG. 7 is a diagram showing a configuration of an image normalization processing system according to a seventh embodiment of the present invention.

A seventh embodiment of the present invention will be explained next. FIG. 7 shows a configuration of an image normalization processing system according to the seventh embodiment of the present invention. The seventh embodiment has the same configuration as the sixth embodiment. However, the parameters P1 are input from the parameter inputting means 16 of the image reading apparatus 10 to the image receiving apparatus 20 in the sixth embodiment, whereas in the seventh embodiment reduced image data S1 generated by normalization processing condition determining means 14 of an image reading apparatus 10 upon determination of a normalization processing condition J1 are input without accompanying parameters P1 to normalization processing condition inputting means 24 of an image receiving apparatus 20. When a condition change is instructed, the normalization processing condition inputting means 24 changes the normalization processing condition J1 based on the reduced image data S1 in order to obtain a normalization processing condition J2. In the seventh embodiment, parameters for obtaining the normalization processing condition J2 are retained within the image receiving apparatus 20.

In the seventh embodiment, normalized image data D2 are normally obtained by carrying out normalization processing on image data D1 under the normalization processing condition J1 output from normalization processing condition outputting means 18. When a condition change command H1 is issued from condition changing means 28, the normalization processing condition J1 output from the normalization processing condition inputting means 24 is changed in response to the condition change command H1, based on the reduced image data S1 and the normalization processing condition determining parameters retained in the image receiving apparatus 20 and the normalization processing condition J2 is obtained. Normalization processing executing means 26 executes the normalization processing on the image data D1 under the changed normalization processing condition J2 to obtain the normalized image data D2.

Therefore, in the seventh embodiment, when the normalization processing executed under the normalization processing condition J1 has a problem, the problem is solved and the normalization processing condition J1 is changed to the normalization processing condition J2 different from the normalization processing condition J1, as in the first embodiment. The normalization processing can then be carried out again using the normalization processing condition J2 having been changed, and the normalized image data that has been subjected to appropriate normalization processing can be output from post-normalization processing image outputting means 30. Furthermore, in the seventh embodiment, since it is not necessary for the reduced image data S1 to be generated from the image data D1 upon determination of the normalization processing condition J2, an operation time for obtaining the normalization processing condition J2 can be shortened.

Figure 8:
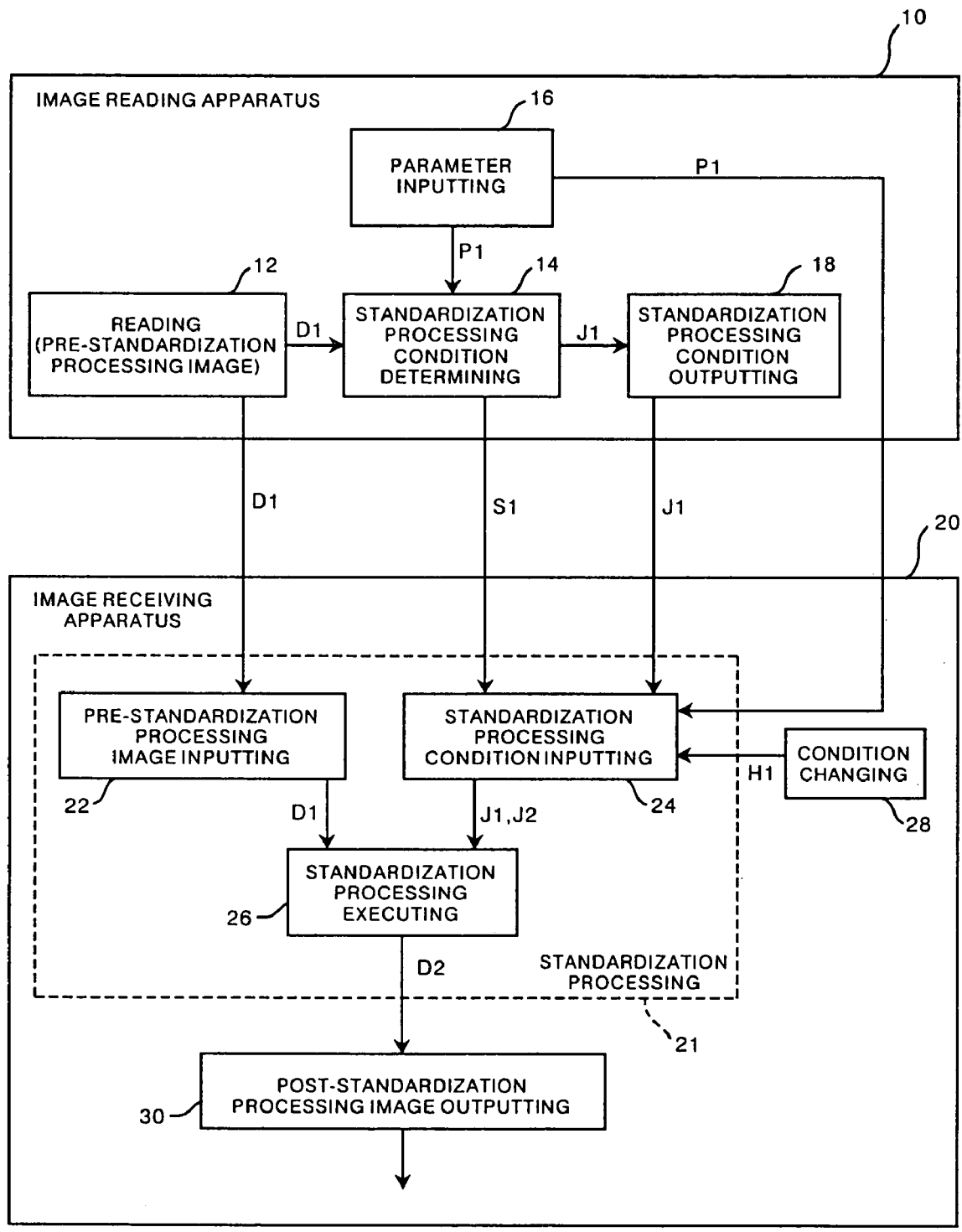
FIG. 8 is a diagram showing a configuration of an image normalization processing system according to an eighth embodiment of the present invention.

An eighth embodiment of the present invention will be explained next. FIG. 8 shows a configuration of an image normalization processing system according to the eighth embodiment of the present invention. The eighth embodiment has the same configuration as the seventh embodiment. However, parameters P1 output from parameter inputting means 16 of an image reading apparatus 10 are input to normalization processing condition determining means 24 of an image receiving apparatus 20 and the normalization processing condition determining means 24 changes a normalization processing condition J1 based on reduced image data S1 and the parameters P1 to obtain a normalization processing condition J2 when a condition change command H1 is issued.

In the eighth embodiment, normalized image data D2 are normally obtained by carrying out normalization processing on the image data D1 under the normalization processing condition J1 output from normalization processing condition outputting means 18. When a condition change command H1 is issued from condition changing means 28, the normalization processing condition inputting means 24 changes the normalization processing condition J1 to be output therefrom in response to the condition change command H1, based on the reduced image data S1 and the parameters P1 input to the image receiving apparatus 20, and the normalization processing condition J2 is obtained. Normalization processing executing means 26 executes the normalization processing on the image data D1 under the changed normalization processing condition J2 to obtain the normalized image data D2.

Therefore, in the eighth embodiment, when the normalization processing executed under the normalization processing condition J1 has a problem, the problem is solved and the normalization processing condition J1 is changed to the normalization processing condition J2 different from the normalization processing condition J1, as in the first embodiment. The normalization processing can be carried out again using the changed normalization processing condition J2, and the normalized image data D2 that has been subjected to appropriate normalization processing can be output from post-normalization processing image outputting means 30. Furthermore, in the eighth embodiment, since it is not necessary for the reduced image data S1 to be generated from the image data D1, an operation time for determination of the normalization processing condition J2 by the normalization processing condition determining means 24 can be shortened. Moreover, in the eighth embodiment, it is not necessary for the image receiving apparatus 20 to retain the parameters for determining the normalization processing condition. Therefore, means for storing the parameters can be saved and the configuration of the image receiving apparatus 20 becomes simpler.

In the above-described first to eighth embodiments, whether or not the normalization processing condition J1 determined by the normalization processing condition determining means 14 of the image reading apparatus 10 is within the predetermined range may be judged. Normalization processing is carried out on the image data D1 under the normalization processing condition J1 to obtain normalized image data D3 output to the image receiving apparatus 20 when the normalization processing condition J1 is within the predetermined range. When the normalization processing condition is not within the predetermined range, as in the first to eighth embodiments, the image data D1, the normalization processing condition J1, the reduced image data S1, and/or the parameters P1 may be output to the image receiving apparatus 20. Hereinafter, an embodiment wherein the image reading apparatus 10 judges whether or not the normalization processing condition J1 is within the predetermined range is explained in accordance with the eighth embodiment, as a ninth embodiment of the present invention.

Figure 9:
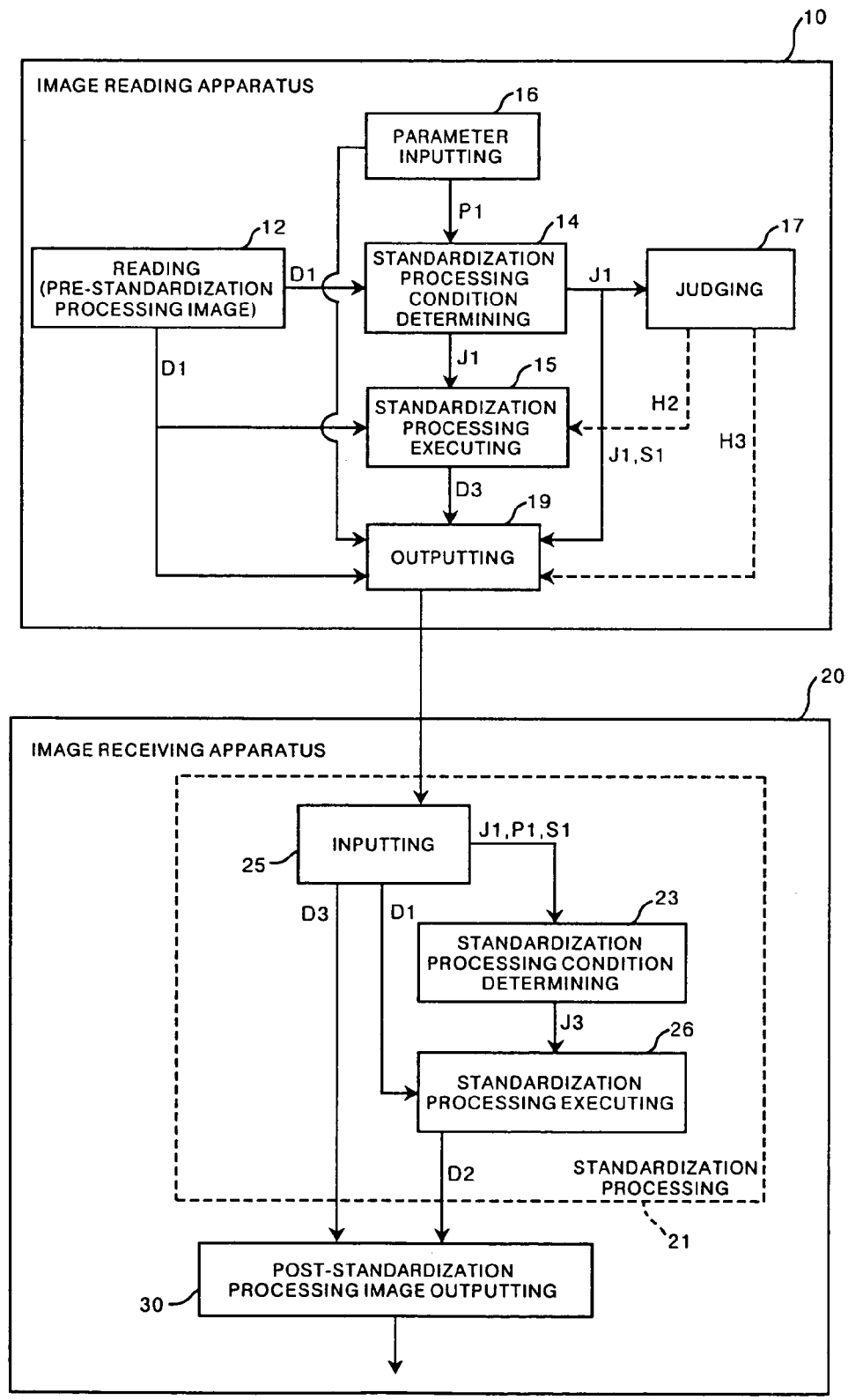
FIG. 9 is a diagram showing a configuration of an image normalization processing system according to a ninth embodiment of the present invention.

FIG. 9 shows a configuration of an image normalization processing system according to the ninth embodiment of the present invention. As shown in FIG. 9, the ninth embodiment comprises an image reading apparatus 10 and an image receiving apparatus 20 both of which are connected to each other, as in the eighth embodiment.

The image reading apparatus 10 comprises reading means 12, normalization processing condition determining means 14, parameter inputting means 16, and normalization processing condition outputting means 18. In addition to these means, the image reading apparatus 10 includes judging means 17 for judging whether or not a normalization processing condition J1 determined by the normalization processing condition determining means 14 is within a predetermined range, normalization processing executing means 15 for executing normalization processing on image data D1 under the normalization processing condition J1 to obtain normalized image data D3 when the normalization processing condition J1 has been judged to be within the predetermined range by the judging means 17, and outputting means 19 for selectively outputting to the image receiving apparatus 20 normalized image data D3, the image data D1, the normalization processing condition J1, reduced image data S1 generated by normalization processing condition determining means 14, and parameters P1 output from the parameter inputting means 16, in response to the judgment result by the judging means 17.

The image receiving apparatus 20 comprises normalization processing means 21 including inputting means 25 for inputting the image data D1 and the like output from the outputting means 19 of the image reading apparatus 10, normalization processing condition determining means 23, normalization processing executing means 26, and post-normalization processing image outputting means 30.

An operation of the image normalization processing system according to the ninth embodiment will be explained below. The image data D1 are acquired by the reading means 12 of the image reading apparatus 10, and are input to the normalization processing condition determining means 14, normalization processing executing means 15, and outputting means 19. The normalization processing condition determining means 14 determines the normalization processing condition J1 based on the parameters P1 input from the parameter inputting means 16. The normalization processing condition J1 is input to the judging means 17.

In the judging means 17, whether or not the normalization processing condition J1 is within the predetermined range is judged. In other words, whether or not an area of interest in the image is in a desired density range if normalization processing is executed on the image data D1 under the normalization processing condition J1 is judged. When the normalization processing condition J1 has been judged to be in the predetermined range, the judging means 17 issues a command H2 to the normalization processing executing means 15, and the normalization processing executing means 15 carries out normalization processing in response to the command H2 on the image data D1 under the normalization processing condition J1 to obtain the normalized image data D3. The normalized image data D3 are output from the outputting means 19 to the inputting means 25 of the image receiving apparatus 20. In the image receiving apparatus 20, the normalized image data D3 are input to the post-normalization processing image outputting means 30 and output therefrom to image processing means which is not shown.

Meanwhile, when the normalization processing condition J1 has been judged to be out of the predetermined range, the image data D1, the normalization processing condition J1, the reduced image data S1, and the parameters P1 are input to the outputting means 19 and a command H3 instructing output of these is also input from the judging means 17 to the outputting means 19. These are input from the outputting means 19 to the inputting means 25 of the image receiving apparatus 20. The normalization processing condition determining means 23 determines a normalization processing condition J3 different from the normalization processing condition J1 based on the reduced image data S1 and the parameters P1. The normalization processing executing means 26 carries out normalization processing on the image data D1 under the normalization processing condition J3 to obtain normalized image data D2. The normalized image data D2 are output via the post-normalization processing image outputting means 30 to the image processing means which is not shown. In this case, normalization processing may be carried out on the image data D1 under the input normalization processing condition J1 so that a visible image of the image data that have been subjected to normalization processing is confirmed. When the density range of the image is a desired one, the image data on which the normalization processing has been carried out under the normalization processing condition J1 may be output from the post-normalization processing image outputting means 30 without finding the normalization processing condition J3 different from the normalization processing condition.

As has been described above, in the ninth embodiment, only when the normalization processing condition J1 is within the predetermined range, are the normalized image data D3 obtained by the image reading apparatus 10 input to the image receiving apparatus 20. Therefore, the image data D1 before normalization processing, the normalization processing condition J1, the reduced image data S1, and the parameters P1 are not input when the normalization processing needs no change, and data can be transferred efficiently. Furthermore, the image data D1, the normalization processing condition J1, the reduced image data S1, and the parameters P1 are only input to the image receiving apparatus when the normalization processing condition J1 is not within the predetermined range. Therefore, the image receiving apparatus 20 can solve the problem in the normalization processing.

Figure 10:
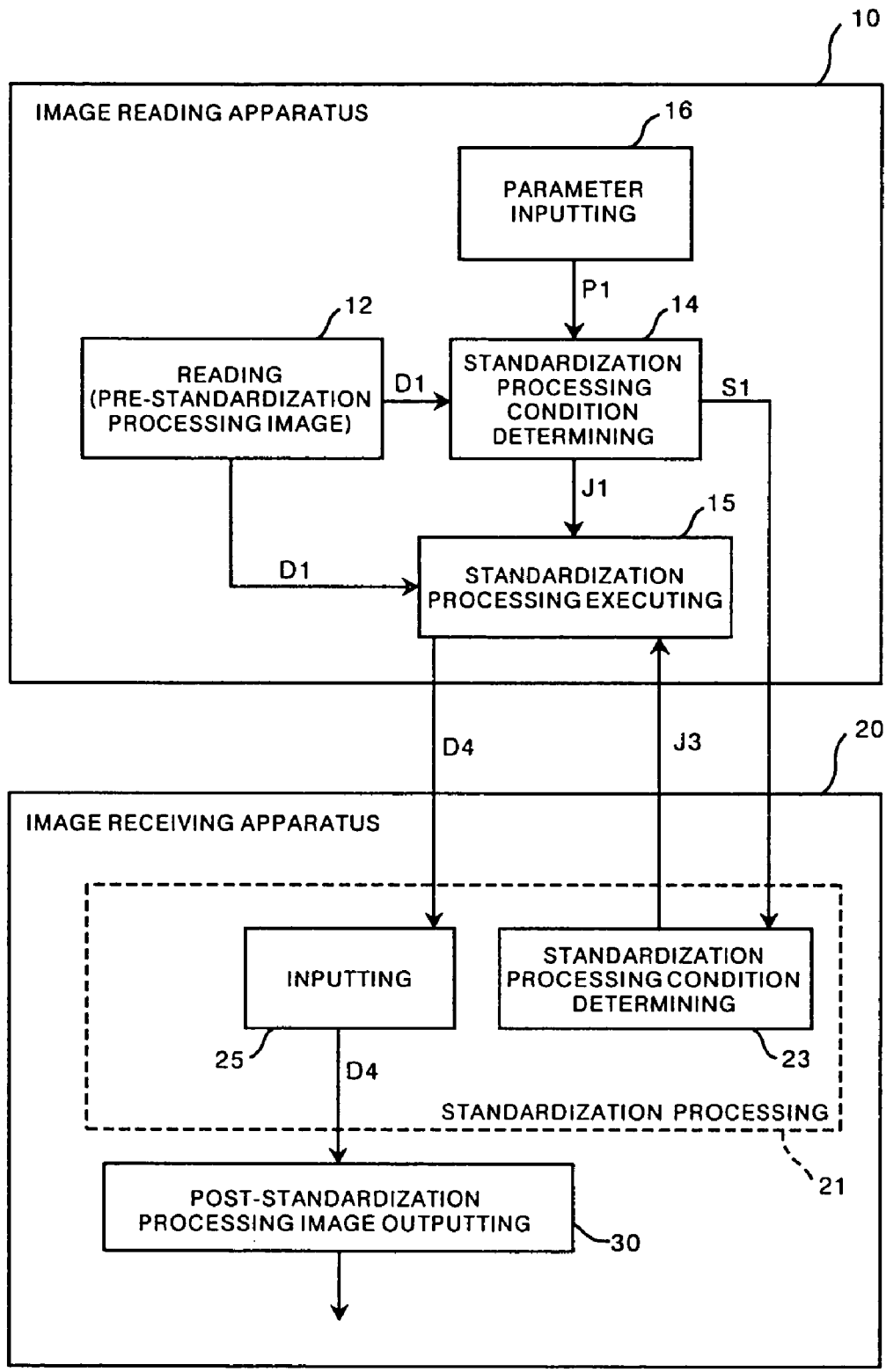
FIG. 10 is a diagram showing a configuration of an image normalization processing system according to a tenth embodiment of the present invention.

A tenth embodiment of the present invention will be explained next. FIG. 10 shows a configuration of an image normalization processing system according to the tenth embodiment of the present invention. As shown in FIG. 10, the tenth embodiment comprises an image reading apparatus 10 and an image receiving apparatus 20, both of which are connected to each other, as in the other embodiments described above. The image reading apparatus 10 comprises reading means 12, normalization processing condition determining means 14, and parameter inputting means 16. The image reading apparatus 10 further comprises normalization processing executing means 15 for carrying out normalization processing on image data D1 under a normalization processing condition J2 determined in the image receiving apparatus 20, as will be described later to obtain normalized image data D4 and for outputting the normalized image data D4 to the image receiving apparatus 20. Reduced image data S1 which are generated when the normalization processing condition J1 is determined by the normalization processing condition determining means 14 are also output to the image receiving apparatus 20.

The image receiving apparatus 20 comprises normalization processing means 21 including normalization processing condition determining means 23 for determining a normalization processing condition J3 for the image data D1 based on the reduced image data S1 output from the image reading apparatus 10, and inputting means 25 for inputting the normalized image data D4 output from the image reading apparatus 10, and post-normalization processing image outputting means 30. In the tenth embodiment, parameters for determination of a normalization processing condition are retained in the image receiving apparatus 20, as in the parameter inputting means 16 in the image reading apparatus 10.

An operation of the image normalization processing system according to the tenth embodiment will be explained below. The image data D1 are obtained by the reading means 12 of the image reading apparatus 10, and are input to the normalization processing condition determining means 14 and the normalization processing executing means 15. The normalization processing condition determining means 14 determines the normalization processing condition J1 based on the parameters P1 input from the parameter inputting means 16. At this time, the reduced image data S1 generated from the image data D1 are output to the image receiving apparatus 20.

The normalization processing condition determining means 23 of the image receiving apparatus 20 determines the normalization processing condition J3 based on the reduced image data S1 output from the image reading apparatus 10. The normalization processing condition J3 can be the same as the normalization processing condition J1. The normalization processing condition J3 is input to the normalization processing executing means 15 of the image reading apparatus 10. In the normalization processing executing means 15, normalization processing is carried out on the image data D1 under the normalization processing condition J3 to obtain the normalized image data D4, and the normalized image data d4 are output to the inputting means 25 of the image receiving apparatus 20. The inputting means 25 inputs the normalized image data D3 to the post-normalized image outputting means 30 and the normalized image data D3 are output therefrom to image processing means or the like.

As has been described above, in the tenth embodiment, only the reduced image data S1 are output from the image reading apparatus 10 to the image receiving apparatus 20, and normalization processing is carried out on the image data D1 by the image reading apparatus 10 under the normalization processing condition J3 determined by the image receiving apparatus 20. Therefore, the image receiving apparatus 20 does not need to comprise either memory for storing the normalized image data or normalization processing executing means for carrying out normalization processing, which leads to a simpler configuration of the image receiving apparatus 20. Furthermore, since only the reduced image data S1 having smaller data size are first transferred from the image reading apparatus 10, data transfer time can be shortened and efficient processing can be carried out. Moreover, the image receiving apparatus 20 can appropriately change the normalization processing condition. As a result, a medical network system with improved convenience can be realized.

Figure 11:
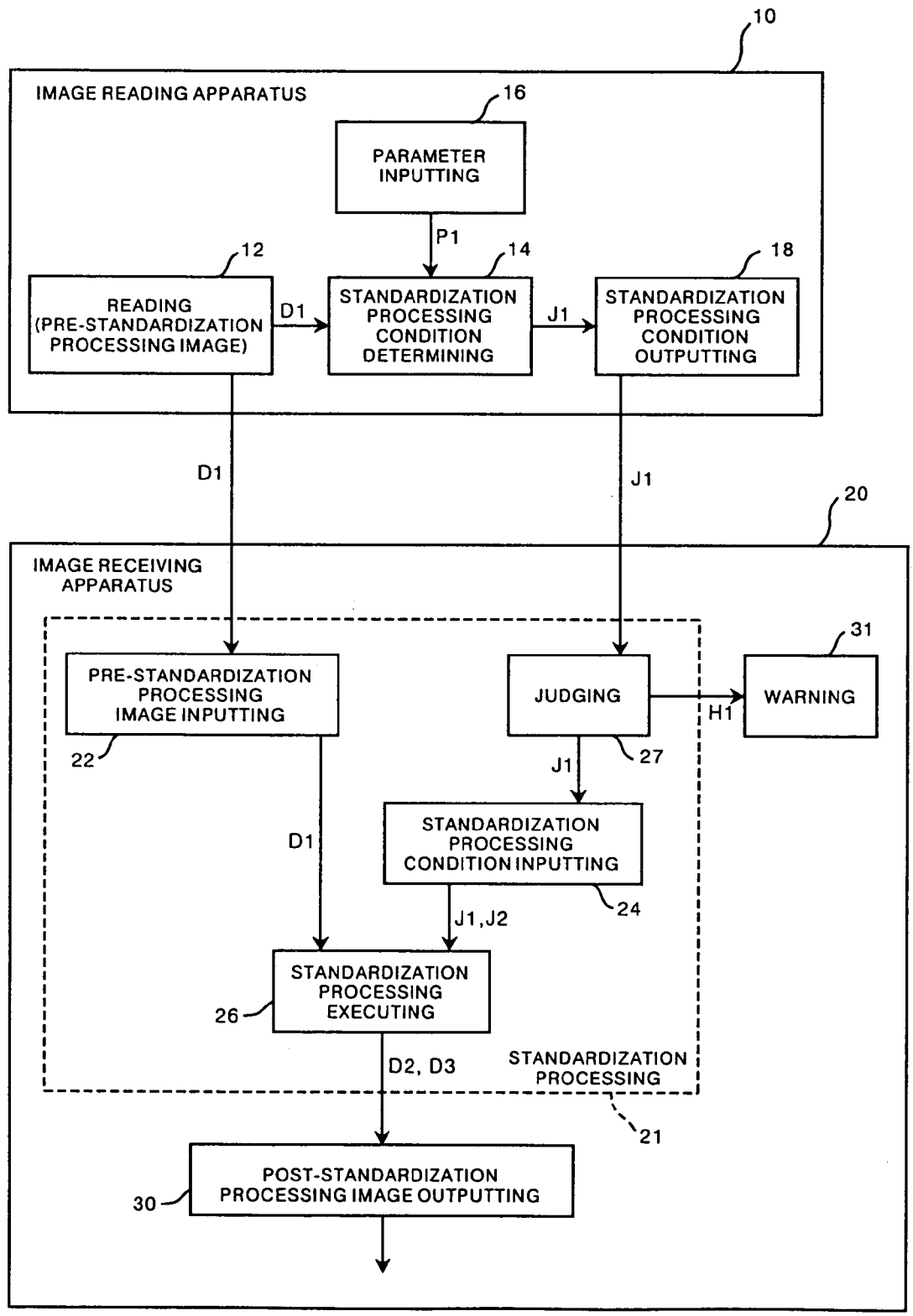
FIG. 11 is a diagram showing a configuration of an image normalization processing system according to an eleventh embodiment of the present invention.

An eleventh embodiment of the present invention will be explained next. FIG. 11 shows a configuration of an image normalization processing system according to the eleventh embodiment of the present invention. As shown in FIG. 11, the eleventh embodiment comprises an image reading apparatus 10 and an image receiving apparatus 20 both of which are connected to each other, as in the above embodiments.

The image reading apparatus 10 comprises reading means 12, normalization processing condition determining means 14, parameter inputting means 16, and normalization processing condition outputting means 18, and outputs image data D1 and a normalization processing condition J1 to the image receiving apparatus 20, similarly to the first embodiment.

The image receiving apparatus 20 comprises normalization processing means 21 including pre-normalization processing image inputting means 22, normalization processing condition inputting means 24, normalization processing executing means 26, judging means 27, post-normalization processing image outputting means 30, and warning means 31 which will be described later. The judging means 27 judges whether or not the normalization processing condition J1 input to the image receiving apparatus 20 is within a predetermined range, and the normalization processing condition inputting means 24 outputs the normalization processing condition J1 to the normalization processing executing means 26 when the normalization processing condition J1 has been judged to be in the predetermined range. Meanwhile, when the judging means has judged that normalization processing condition J1 is not within the predetermined range, the normalization processing condition J1 is changed to a normalization processing condition J2 having a different parameter value, and the normalization processing condition inputting means 24 outputs the normalization processing condition J2 to the normalization processing executing means 26, as in the first embodiment. The warning means 31 issues a warning notifying cancellation of normalization processing under the normalization processing condition J1, when the normalization processing condition J1 has been judged to be out of the predetermined range by the judging means 27. As the warning, cancellation of the normalization processing may be displayed on display means (not shown in FIG. 11) of the image receiving apparatus 20 or may be notified by an audio message or an alarm.

An operation of the image normalization processing system according to the eleventh embodiment will be explained next. The image data D1 are obtained by the reading means 12 of the image reading apparatus 10, and are input to the normalization processing condition determining means 14. The normalization processing condition determining means 14 determines the normalization processing condition J1 based on the parameters P1 input thereto from the parameter inputting means 16. The normalization processing condition J1 is then input to the normalization processing condition outputting means 18 and output therefrom to the image receiving apparatus 20. The image data D1 are also output to the image receiving apparatus 20.

In the image receiving apparatus 20, the normalization processing condition J1 is input to the judging means 27, and whether or not the normalization processing condition J1 is with in a predetermined range is judged thereby. In other words, whether or not an area of interest in the image is in a desired density range if normalization processing is executed on the image data D1 under the normalization processing condition J1 is judged. When the normalization processing condition J1 has been judged to be in the predetermined range, the judgment result is input to the normalization processing condition inputting means 24 and the normalization processing condition J1 is input therefrom to the normalization processing executing means 26. The normalization processing executing means 26 carries out normalization processing on the image data D1 under the normalization processing condition J1 to obtain normalized image data D2. The normalized image data D2 are then output from the post-normalization processing image outputting means 30.

Meanwhile, when the normalization processing condition J1 has been judged to be out of the predetermined range, the judgment result is input to the normalization processing condition inputting means 24. In response to this notification, a parameter value of the normalization processing condition J1 is changed and the normalization processing condition J2 is obtained. The normalization processing condition J2 is then input from the normalization processing condition determining means 24 to the normalization processing executing means 26. At the same time, a warning notifying cancellation of the normalization processing under the normalization processing condition J1 is issued from the warning means 31. The normalization processing executing means 26 carries out normalization processing on the image data D1 under the normalization processing condition J2 to obtain normalized image data D3. The normalized image data D3 are output from the post-normalization processing image outputting means 30.

As has been described above, in the eleventh embodiment, the image data D1 and the normalization processing condition J1 are input from the image reading apparatus 10 to the image receiving apparatus 20, and in the image receiving apparatus 20, whether or not the normalization processing condition J1 is within the predetermined range is judged. When the normalization processing condition is within the predetermined range, normalization processing is carried out on the image data d1 under the normalization processing condition J1, and otherwise normalization processing is carried out under the changed normalization processing condition J2. In this manner, no normalization processing under a problematic normalization processing condition is carried out and unnecessary normalization processing is prevented from being carried out.

Furthermore, by issuing a warning notifying cancellation of normalization processing under the normalization processing condition J1, an operator can be made aware of the cancellation.

In the above-described eleventh embodiment, the warning is issued in the case where the normalization processing under the normalization processing condition J1 has been canceled. However, the warning is not necessarily needed. Furthermore, when the normalization processing condition J1 is not within the predetermined range, normalization processing condition J2 is found and normalization processing under J2 is carried out. However, the normalization processing condition J2 may be found after an operator's instruction of change.

In the above explanation, the image reading apparatus 10 and the image receiving apparatus 20 are separate from each other. However, the present invention is not limited to this example, and is applicable to a CR apparatus and the like which has the components of both the image reading apparatus 10 and the image receiving apparatus 20.

What is claimed is:

1. An image normalization processing system comprising:
   an image reading apparatus including reading means for reading an image to obtain image data representing the image and reading side normalization processing condition determining means for determining a normalization processing condition for the image read by the reading means, the image reading apparatus outputting the image data and the normalization processing condition; and
   an image receiving apparatus connected to the image reading apparatus and including receiving side normalization processing condition determining means for determining a normalization processing condition for the image based on the image data and normalization processing means for carrying out normalization processing using the normalization processing condition determined by the receiving side normalization processing condition determining means or the normalization processing condition determined on the reading side, on the image data.

2. The image normalization processing system of claim 1, wherein the image read by the reading means is a radiation image stored on a stimulable phosphor sheet.

3. The image processing system of claim 1, wherein the normalization processing condition determined at the reading side normalization processing condition determining means adjusts the image data read by the reading means to an input signal range of an image processing means.

4. The image processing system of claim 3, wherein the normalization processing condition adjusts the image data so that a visible image of the image data has a predetermined density range.

5. The image processing system of claim 1, wherein the normalization processing condition is gain and a data range of the reading means.

6. An image normalization processing system comprising:
   an image reading apparatus including reading means for reading an image to obtain image data representing the image and reading side normalization processing condition determining means for determining a normalization processing condition for the image read by the reading means, the image reading apparatus outputting the image data, the normalization processing condition and reduced image data generated from the image data by the reading side normalization processing condition determining means; and
   an image receiving apparatus connected to the image reading apparatus and including receiving side normalization processing condition determining means for determining a normalization processing condition for the image based on the reduced image data, and normalization processing means for carrying out normalization processing on the image data under the normalization processing condition determined by the receiving side normalization processing condition determining means or the normalization processing condition determined on the reading side.

7. The image normalization processing system of claim 6, wherein the image read by the reading means is a radiation image stored on a stimulable phosphor sheet.

8. An image normalization processing system comprising:
   an image reading apparatus including reading means for reading an image to obtain image data representing the image and reading side normalization processing condition determining means for determining a normalization processing condition for the image read by the reading means, the image reading apparatus outputting the image data and the normalization processing condition; and
   an image receiving apparatus connected to the image reading apparatus and including normalization processing means for carrying out normalization processing on the image data under the normalization processing condition and condition changing means for changing the normalization processing condition; wherein
   the normalization processing means carries out normalization processing on the image data under a normalization processing condition changed by the condition changing means, or the normalization processing condition directly in association with the normalization processing means.

9. The image normalization processing system of claim 8, wherein the image read by the reading means is a radiation image stored on a stimulable phosphor sheet.

10. An image normalization processing system comprising:
    an image reading apparatus including reading means for reading an image to obtain image data representing the image and reading side normalization processing condition determining means for determining a normalization processing condition for the image read by the reading means, the image reading apparatus outputting the image data the normalization processing condition and a parameter for determining the normalization processing condition; and
    an image receiving apparatus connected to the image reading apparatus and including receiving side normalization processing condition determining means for determining a normalization processing condition for the image based on the image data and the parameter, and normalization processing means for carrying out normalization processing on the image data under the normalization processing condition determined by the receiving side normalization processing condition determining means or the normalization processing condition determined on the reading side.

11. The image normalization processing system of claim 10, wherein the image read by the reading means is a radiation image stored on a stimulable phosphor sheet.

12. An image normalization processing system comprising:
    an image reading apparatus including reading means for reading an image to obtain image data representing the image and reading side normalization processing condition determining means for determining a normalization processing condition for the image read by the reading means, the image reading apparatus outputting the image data, reduced image data generated from the image data by the reading side normalization processing condition determining means, and a parameter for determining the normalization processing condition; and
    an image receiving apparatus connected to the image reading apparatus and including receiving side normalization processing condition determining means for determining a normalization processing condition of the image based on the reduced image data and the parameter, and normalization processing means for carrying out normalization processing on the image data under the normalization processing condition determined by the receiving side normalization processing condition determining means.

13. An image normalization processing system comprising:
an image reading apparatus including reading means for reading an image to obtain image data representing the image and reading side normalization processing condition determining means for determining a normalization processing condition for the image read by the reading means, the image reading apparatus outputting the image data, the normalization processing condition, and a parameter for determining the normalization processing condition; and
an image receiving apparatus connected to the image reading apparatus and including normalization processing means for carrying out normalization processing on the image data under the normalization processing condition and condition changing means for changing the normalization processing condition based on the parameter; wherein
the normalization processing means carries out normalization processing on the image data under a normalization processing condition changed by the condition changing means, or the normalization processing condition directly in association with the normalization processing means.

14. The image normalization processing system of claim 13, wherein the image read by the reading means is a radiation image stored on a stimulable phosphor sheet.

15. An image normalization processing system comprising:
an image reading apparatus including reading means for reading an image to obtain image data representing the image and reading side normalization processing condition determining means for determining a normalization processing condition for the image read by the reading means, the image reading apparatus outputting the image data, the normalization processing condition, and reduced image data generated from the image data by the reading side normalization processing condition determining means; and
an image receiving apparatus connected to the image reading apparatus and including normalization processing means for carrying out normalization processing on the image data under the normalization processing condition and condition changing means for changing the normalization processing condition based on the reduced image data, wherein
the normalization processing means carries out normalization processing on the image data under a normalization processing condition changed by the condition changing means
or the normalization processing condition determined on the reading side.

16. An image normalization processing system comprising:
an image reading apparatus including reading means for reading an image to obtain image data representing the image and reading side normalization processing condition determining means for determining a normalization processing condition for the image read by the reading means, the image reading apparatus outputting the image data, the normalization processing condition, reduced image data generated from the image data by the reading side normalization processing condition determining means, and a parameter for determining the normalization processing condition; and
an image receiving apparatus connected to the image reading apparatus and including normalization processing means for carrying out normalization processing on the image data under the normalization processing condition and condition changing means for changing the normalization processing condition based on the reduced image data and the parameter, wherein
the normalization processing means carries out normalization processing on the image data under a normalization processing condition changed by the condition changing means, or the normalization processing condition directly in association with the normalization processing means.

17. An image normalization processing system comprising:
an image reading apparatus including reading means for reading an image to obtain image data representing the image, reading side normalization processing condition determining means for determining a normalization processing condition for the image read by the reading means, reading side normalization processing means for carrying out normalization processing on the image data under the normalization processing condition determined by the reading side normalization processing condition determining means to obtain normalized image data, and judging means for judging whether or not the normalization processing condition is within a predetermined range, the image reading apparatus outputting the normalized image data in the case where the normalization processing condition has been judged by the judging means to be in the predetermined range and outputting the image data in the case where the normalization processing condition has been judged by the judging means to be not in the predetermined range; and
image receiving apparatus connected to the image reading apparatus and including receiving side normalization processing condition determining means for determining a normalization processing condition for the image based on the image data, and receiving side normalization processing means for carrying out normalization processing on the image data under the normalization processing condition determined by the receiving side normalization processing condition determining means, the receiving side normalization processing condition determining means and the receiving side normalization processing means respectively carrying out the determination of the normalization processing condition and the normalization processing in the case where the image data have been received by the image receiving apparatus.

18. An image normalization processing system comprising:
image reading apparatus including reading means for reading an image to obtain image data representing the image, reading side normalization processing condition determining means for determining a normalization processing condition for the image read by the reading means, reading side normalization processing means for carrying out normalization processing on the image data under the normalization processing condition determined by the reading side normalization processing condition determining means to obtain normalized image data, and judging means for judging whether or not the normalization processing condition is within a predetermined range, the image reading apparatus outputting the normalized image data in the case where the normalization processing condition has been judged by the judging means to be in the predetermined range, and outputting the image data, and reduced image data generated from the image data by the reading side normalization processing condition determining means in the case where the normalization processing condition has been judged to be not in the predetermined range; and image receiving apparatus connected to the image reading apparatus and including receiving side normalization processing condition determining means for determining a normalization processing condition for the image based on the reduced image data, and receiving side normalization processing means for carrying out normalization processing on the image data under the normalization processing condition determined by the receiving side normalization processing condition determining means, the receiving side normalization processing condition determining means and the receiving side normalization processing means respectively carrying out the determination of the normalization processing condition and the normalization processing in the case where the image data and the reduced image data have been received by the image receiving apparatus.

19. An image normalization processing system comprising:

an image reading apparatus including reading means for reading an image to obtain image data representing the image, reading side normalization processing condition determining means for determining a normalization processing condition for the image read by the reading means, reading side normalization processing means for carrying out normalization processing on the image data under the normalization processing condition determined by the reading side normalization processing condition determining means to obtain normalized image data, and judging means for judging whether or not the normalization processing condition is within a predetermined range, the image reading apparatus outputting the normalized image data in the case where the normalization processing condition has been judged by the judging means to be in the predetermined range and outputting the image data and the normalization processing condition in the case where the normalization processing condition has been judged by the judging means to be not in the predetermined range; and image receiving apparatus connected to the image reading apparatus and including receiving side normalization processing means for carrying out normalization processing on the image data under the normalization processing condition, and condition changing means for changing the normalization processing condition, wherein the receiving side normalization processing means is capable of carrying out normalization processing on the image data under the normalization processing condition changed by the condition changing means in the case where the image data and the normalization processing condition have been received by the image receiving apparatus.

20. An image normalization processing system comprising:

an image reading apparatus including reading means for reading an image to obtain image data representing the image, reading side normalization processing condition determining means for determining a normalization processing condition for the image read by the reading means, reading side normalization processing means for carrying out normalization processing on the image data under the normalization processing condition determined by the reading side normalization processing condition determining means to obtain normalized image data, and judging means for judging whether or not the normalization processing condition is within a predetermined range, the image reading apparatus outputting the normalized image data in the case where the normalization processing condition has been judged by the judging means to be in the predetermined range and outputting the image data and a parameter for determining the normalization processing condition in the case where the normalization processing condition has been judged by the judging means to be not in the predetermined range; and image receiving apparatus connected to the image reading apparatus and including receiving side normalization processing condition determining means for determining a normalization processing condition for the image based on the image data and the parameter, and receiving side normalization processing means for carrying out normalization processing on the image data under the normalization processing condition determined by the receiving side normalization processing condition determining means, the receiving side normalization processing condition determining means and the receiving side normalization processing means respectively carrying out the determination of the normalization processing condition and the normalization processing in the case where the image data and the parameter have been received by the image receiving apparatus.

21. An image normalization processing system comprising:

an image reading apparatus including reading means for reading an image to obtain image data representing the image, reading side normalization processing condition determining means for determining a normalization processing condition for the image read by the reading means, reading side normalization processing means for carrying out normalization processing on the image data under the normalization processing condition determined by the reading side normalization processing condition determining means to obtain normalized image data, and judging means for judging whether or not the normalization processing condition is within a predetermined range, the image reading apparatus outputting the normalized image data in the case where the normalization processing condition has been judged by the judging means to be in the predetermined range and outputting the image data, reduced image data generated from the image data by the reading side normalization processing condition determining means and a parameter for determining the normalization processing condition in the case where the normalization processing condition has been judged by the judging means to be not in the predetermined range; and image receiving apparatus connected to the image reading apparatus and including receiving side normalization processing condition determining means for determining a normalization processing condition for the image based on the reduced image data and the parameter, and receiving side normalization processing means for carrying out normalization processing on the image data under the normalization processing condition determined by the receiving side normalization processing condition determining means, the receiving side normalization processing condition determining means and the receiving side normalization processing means respectively carrying out the determination of the normalization processing condition and the normalization processing in the case where the image data, the reduced image data, and the parameter have been received by the image receiving apparatus.

22. An image normalization processing system comprising:

an image reading apparatus including reading means for reading an image to obtain image data representing the image, normalization processing condition determining means for determining a normalization processing condition for the image read by the reading means, reading side normalization processing means for carrying out normalization processing on the image data under the normalization processing condition determined by the normalization processing condition determining means to obtain normalized image data, and judging means for judging whether or not the normalization processing condition is within a predetermined range, the image reading apparatus outputting the normalized image data in the case where the normalization processing condition has been judged by the judging means to be in the predetermined range and outputting the image data, the normalization processing condition, and a parameter for determining the normalization processing condition in the case where the normalization processing condition has been judged by the judging means to be not in the predetermined range; and image receiving apparatus connected to the image reading apparatus and including receiving side normalization processing means for carrying out normalization processing on the image data under the normalization processing condition, and condition changing means for changing the normalization processing condition based on the parameter, wherein the receiving side normalization processing means is capable of carrying out normalization processing on the image data under the normalization processing condition changed by the condition changing means in the case where the image data, the normalization processing condition, and the parameter have been received by the image receiving apparatus.

23. An image normalization processing system comprising:

an image reading apparatus including reading means for reading an image to obtain image data representing the image, normalization processing condition determining means for determining a normalization processing condition for the image read by the reading means, reading side normalization processing means for carrying out normalization processing on the image data under the normalization processing condition determined by the normalization processing condition determining means to obtain normalized image data, and judging means for judging whether or not the normalization processing condition is within a predetermined range, the image reading apparatus outputting the normalized image data in the case where the normalization processing condition has been judged by the judging means to be in the predetermined range and outputting the image data, the normalization processing condition, and reduced image data generated from the image data by the normalization processing condition determining means in the case where the normalization processing condition has been judged to be not in the predetermined range by the judging means; and image receiving apparatus connected to the image reading apparatus and including receiving side normalization processing means for carrying out normalization processing on the image data under the normalization processing condition and condition changing means for changing the normalization processing condition based on the reduced image data, wherein the receiving side normalization processing means is capable of carrying out normalization processing on the image data under the normalization processing condition changed by the condition changing means in the case where the image data, the normalization processing condition, and the reduced image data have been received by the image receiving apparatus.

24. An image normalization processing system comprising:

an image reading apparatus including reading means for reading an image to obtain image data representing the image, normalization processing condition determining means for determining a normalization processing condition for the image read by the reading means, reading side normalization processing means for carrying out normalization processing on the image data under the normalization processing condition determined by the normalization processing condition determining means to obtain normalized image data, and judging means for judging whether or not the normalization processing condition is within a predetermined range, the image reading apparatus outputting the normalized image data in the case where the normalization processing condition has been judged to be in the predetermined range by the judging means and outputting the image data, the normalization processing condition, reduced image data generated from the image data by the normalization processing condition determining means, and a parameter for determining the normalization processing condition in the case where the normalization processing condition has been judged by the judging means to be not in the predetermined range; and image receiving apparatus connected to the image reading apparatus and including receiving side normalization processing means for carrying out normalization processing on the image data under the normalization processing condition and condition changing means for changing the normalization processing condition based on the reduced image data and the parameter, wherein the receiving side normalization processing means is capable of carrying out normalization processing on the image data under the normalization processing condition changed by the condition changing means in the case where the image data, the normalization processing condition, the reduced image data, and the parameter have been received by the image receiving apparatus.

25. An image normalization processing system comprising:

an image reading apparatus including reading means for reading an image to obtain image data representing the image, reading side normalization processing condition determining means for determining a first normalization processing condition for the image read by the reading means, and reading side normalization processing means for carrying out normalization processing on the image data, the image reading apparatus outputting reduced image data generated from the image data by the reading side normalization processing condition determining means;

an image receiving apparatus connected to the image reading apparatus and including receiving side normalization processing condition determining means for determining a second normalization processing condition based on the reduced image data, wherein the second normalization processing condition is output to the image reading apparatus and the reading side normalization processing means carries out normalization processing on the image data under the second normalization processing condition to obtain normalized image data to be output to the image receiving apparatus, or the first normalization processing condition directly in association with the normalization processing means.

26. An image normalization processing system comprising:

an image reading apparatus including reading means for reading an image to obtain image data representing the image and reading side normalization processing condition determining means for determining a normalization processing condition for the image read by the reading means, the image reading apparatus outputting the image data and the normalization processing condition; and an image receiving apparatus connected to the image reading apparatus and including judging means for judging whether or not the normalization processing condition is within a predetermined range, normalization processing means for carrying out normalization processing on the image data under the normalization processing condition in the case where the normalization processing condition has been judged to be in the predetermined range, and canceling means for canceling the normalization processing by the normalization processing means under the normalization processing condition in the case where the normalization processing condition has been judged to be not in the predetermined range.

27. An image normalization processing system according to claim 26 further comprising warning means for issuing a warning in the case where the normalization processing has been canceled by the canceling means.

28. An image normalization processing system according to claim 26 further comprising condition changing means for changing the normalization processing condition, wherein the normalization processing condition is changed by the condition changing means and the normalization processing means carries out normalization processing on the image data under the changed normalization processing condition in the case where the normalization processing has been canceled by the canceling means.

29. An image normalization processing system according to claim 27 further comprising condition changing means for changing the normalization processing condition, wherein the normalization processing condition is changed by the condition changing means and the normalization processing means carries out normalization processing on the image data under the changed normalization processing condition in the case where the normalization processing has been canceled by the canceling means.

30. An image output method wherein an image reading apparatus, comprising reading means for reading an image to obtain image data representing the image and normalization processing condition determining means for determining a normalization processing condition for the image read by the reading means, outputs the image data to an image receiving apparatus; wherein, in addition to the image data, at least one of the normalization processing condition, reduced image data generated from the image data by the normalization processing condition determining means, and a parameter for determining the normalization processing condition are output to the image receiving apparatus; and at least one of the normalization processing condition determined on the reading side, the reduced image data generated from the image data by the normalization processing condition determining means, and the parameter for determining the normalization processing condition is used for normalization processing.

31. The image output method of claim 30, wherein the image read by the reading means is a radiation image stored on a stimulable phosphor sheet.

32. An image output method wherein an image reading apparatus, comprising reading means for reading an image to obtain image data representing the image and normalization processing condition determining means for determining a normalization processing condition for the image read by the reading means, outputs the image data to an image receiving apparatus;

wherein whether or not the normalization processing condition is within a predetermined range is judged and in addition to the image data, at least one of the normalization processing condition, reduced image data generated from the image data by the normalization processing condition determining means, and a parameter for determining the normalization processing condition are output to the image receiving apparatus when the normalization processing condition is not within the predetermined range;

wherein at least one of the normalization processing condition determined on the reading side, reduced image data generated from the image data by the normalization processing condition determining means, and a parameter for determining the normalization processing condition is used for normalization processing.

* * * * *